United States Patent
Betts et al.

(10) Patent No.: US 11,893,328 B2
(45) Date of Patent: Feb. 6, 2024

(54) APPARATUS AND METHOD FOR SIMULATING SYSTEMS

(71) Applicant: PREDICTIVEIQ LLC, Boston, MA (US)

(72) Inventors: Daniel Augusto Betts, Parkland, FL (US); Matthew Tilghman, Fort Lauderdale, FL (US); Juan Fernando Betts, Parkland, FL (US)

(73) Assignee: PREDICTIVEIQ LLC, Boston, MA (US)

( * ) Notice: Subject to any disclaimer, the term of this patent is extended or adjusted under 35 U.S.C. 154(b) by 635 days.

(21) Appl. No.: 16/910,721

(22) Filed: Jun. 24, 2020

(65) Prior Publication Data

US 2020/0401748 A1 Dec. 24, 2020

Related U.S. Application Data

(60) Provisional application No. 62/865,513, filed on Jun. 24, 2019.

(51) Int. Cl.
| | |
|---|---|
| *B64F 5/10* | (2017.01) |
| *G06F 30/28* | (2020.01) |
| *G16C 20/10* | (2019.01) |
| *G16C 20/70* | (2019.01) |
| *G06F 30/27* | (2020.01) |
| *G06F 111/10* | (2020.01) |

(52) U.S. Cl.
CPC ............. *G06F 30/28* (2020.01); *G16C 20/10* (2019.02); *G16C 20/70* (2019.02); *G06F 30/27* (2020.01); *G06F 2111/10* (2020.01)

(58) Field of Classification Search
CPC .............. B64F 5/10; B64F 5/60; G06F 21/71
See application file for complete search history.

(56) References Cited

U.S. PATENT DOCUMENTS

| | | | |
|---|---|---|---|
| 2009/0043547 A1 | 2/2009 | Kirby et al. | |
| 2011/0257949 A1 | 10/2011 | Vasudevan et al. | |
| 2015/0242547 A1 | 8/2015 | Phadke et al. | |
| 2017/0286572 A1* | 10/2017 | Hershey | B64F 5/60 |

\* cited by examiner

*Primary Examiner* — Lam S Nguyen
(74) *Attorney, Agent, or Firm* — DUANE MORRIS LLP; Gregory M. Lefkowitz; Joaquin Hernandez

(57) ABSTRACT

This application relates to apparatus and methods for generating, and executing, surrogate models. In some examples, a computing device generates and evaluates correlations between input and output variables for a system to identify highly correlated input and output parameters. In addition, weights for one or more of the parameters may be determined. The computing device identifies a mathematical relationship between input and output variables to generate a physics model. The computing device may also identify other features not captured by the physical relationship that are highly correlated to each other, and generates a feature model that is based on the highly correlated features. The computing device may optimize the feature model based on a culling process that reduces the computational resources required to execute the feature model. The physics model is then combined with the feature model to generate a system output model that can simulate the system.

19 Claims, 8 Drawing Sheets

APPARATUS AND METHOD FOR SIMULATING SYSTEMS

CROSS-REFERENCE TO RELATED APPLICATIONS

This application claims the benefit of U.S. Provisional Patent Application No. 62/865,513 filed on Jun. 24, 2019, which is hereby incorporated by reference in its entirety.

FIELD OF THE INVENTION

The disclosure relates generally to electronic simulation systems and, more specifically, to electronic simulation systems to predict system reliability and performance.

BACKGROUND

Emulators, Response Surface Models (RSMs), and Reduced Order Models (ROMs) are a class of predictive analytics methods (collectively referred to as Surrogate Models or "SMs") that can predict an output of a system based on a set of input parameters. Outputs can include the performance of a machine, the failure rate of a component, or a classification. SMs are typically used to predict system outcomes before they occur.

SUMMARY

In some examples, a computing device configured to identify a mathematical representation of a system, and determine correlations between system input data and system output data of the system. The computing device is also configured to identify at least a portion of the system input data based on the correlations. Further, the computing device is configured to generate a first feature function with function input data based on the identified portion of the system input data, wherein the original feature function characterizes at least a portion of the system. The computing device is also configured to generate at least a second feature function with function input data based on a portion of the identified portion of the system input data for the first feature function. The computing device is further configured to determine an estimated error for each of the first feature function and the at least second feature function. The computing device is also configured to determine a final feature function based on the determined estimated errors. The computing device is further configured to generate a surrogate model for the system based on the mathematical representation of the system and the determined feature function.

In some examples, a non-transitory computer readable medium has instructions stored thereon. The instructions, when executed by at least one processor, cause a device to perform operations that include identifying a mathematical representation of a system, and determining correlations between system input data and system output data of the system. The operations also include identifying at least a portion of the system input data based on the correlations. Further, the operations include generating a first feature function with function input data based on the identified portion of the system input data, wherein the original feature function characterizes at least a portion of the system. The operations also include generating at least a second feature function with function input data based on a portion of the identified portion of the system input data for the first feature function. The operations further include determining an estimated error for each of the first feature function and the at least second feature function. Further, the operations include determining a final feature function based on the determined estimated errors. The operations also include generating a surrogate model for the system based on the mathematical representation of the system and the determined feature function.

In some examples, a system includes a computing device configured to receive sensor data from an apparatus. The computing device is also configured to execute a surrogate model for the system, where the surrogate model is based on a mathematical representation of the system and a feature function. The computing device is further configured to determine a system state for the system based on the received sensor data and execution of the surrogate model, and provide for display the system state. In some examples, the computing device is configured to predict a future state of a component of the system based on the received sensor data and execution of the surrogate model.

In some examples, the computing device is configured to determine correlations between system input data and system output data of the system, and identify at least a portion of the system input data based on the correlations. The computing device is also configured to generate a first feature function with function input data based on the identified portion of the system input data, where the original feature function characterizes at least a portion of the system. The computing device is further configured to generate at least a second feature function with function input data based on a portion of the identified portion of the system input data for the first feature function. The computing device is also configured to determine an estimated error for each of the first feature function and the at least second feature function. Further, the computing device is configured to determine a final feature function based on the determined estimated errors. The computing device is also configured to generate the surrogate model for the system based on the mathematical representation of the system and the determined final feature function.

BRIEF DESCRIPTION OF THE DRAWINGS

The features and advantages of the present disclosures will be more fully disclosed in, or rendered obvious by the following detailed descriptions of example embodiments. The detailed descriptions of the example embodiments are to be considered together with the accompanying drawings wherein like numbers refer to like parts and further wherein.

DETAILED DESCRIPTION

Figure 1:
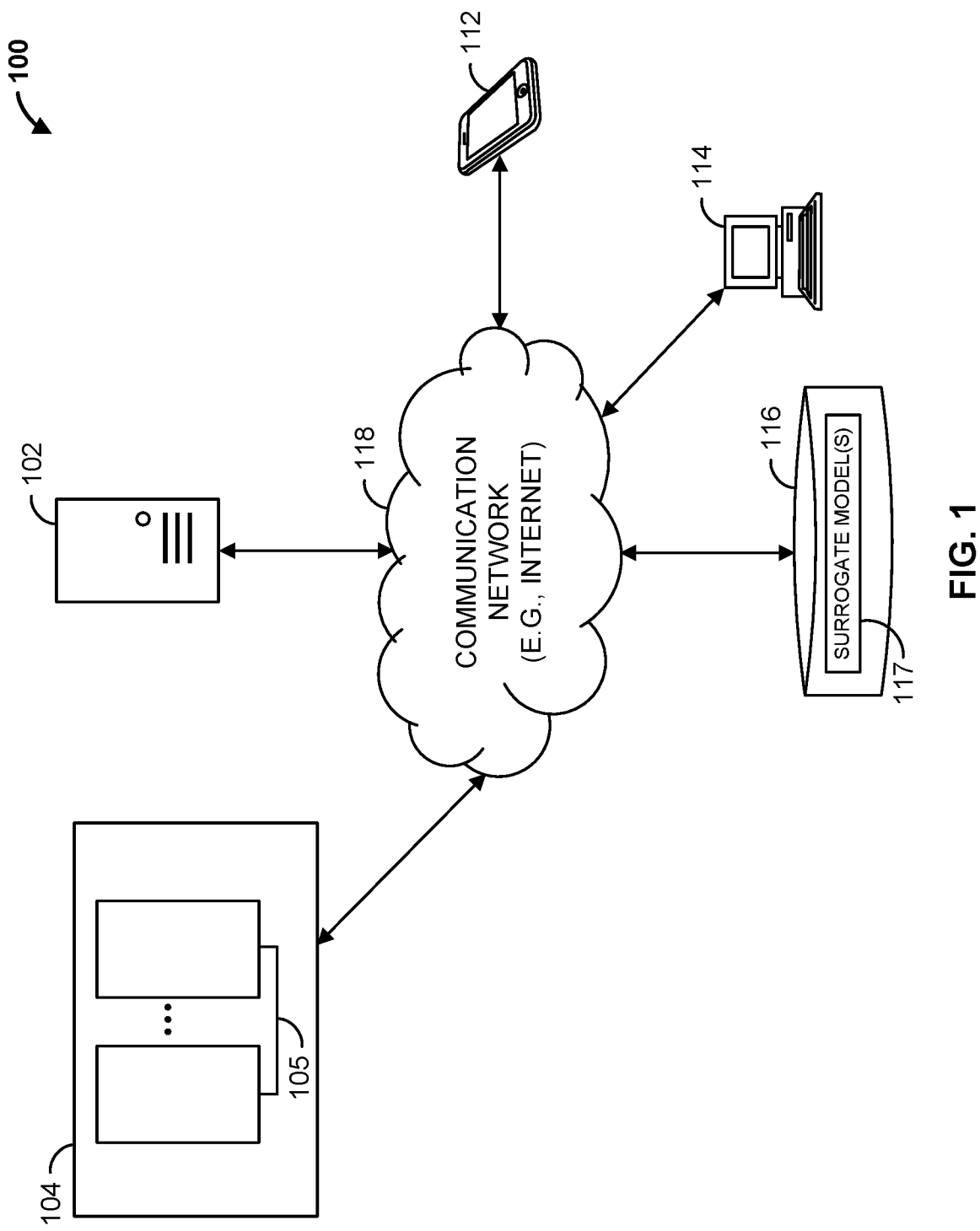
FIG. 1 is a block diagram of a surrogate model system in accordance with some embodiments.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

Turning to the drawings, FIG. 1 illustrates a block diagram of a surrogate model system 100 that includes a surrogate model computing device 102, a system 104, database 116, and multiple customer computing devices 112, 114 communicatively coupled over network 118. Surrogate model computing device 102 and multiple customer computing devices 112, 114 can each be any suitable computing device that includes any hardware or hardware and software combination for processing and handling information. For example, each of surrogate model computing device 102 and multiple customer computing devices 112, 114 can include one or more processors, one or more field-programmable gate arrays (FPGAs), one or more application-specific integrated circuits (ASICs), one or more state machines, digital circuitry, or any other suitable circuitry. In addition, each can transmit data to, and receive data from, communication network 118.

Surrogate model computing device 102 can be, for example, a computer, a workstation, a laptop, a server such as a cloud-based server or an application server, or any other suitable computing device.

Figure 2:
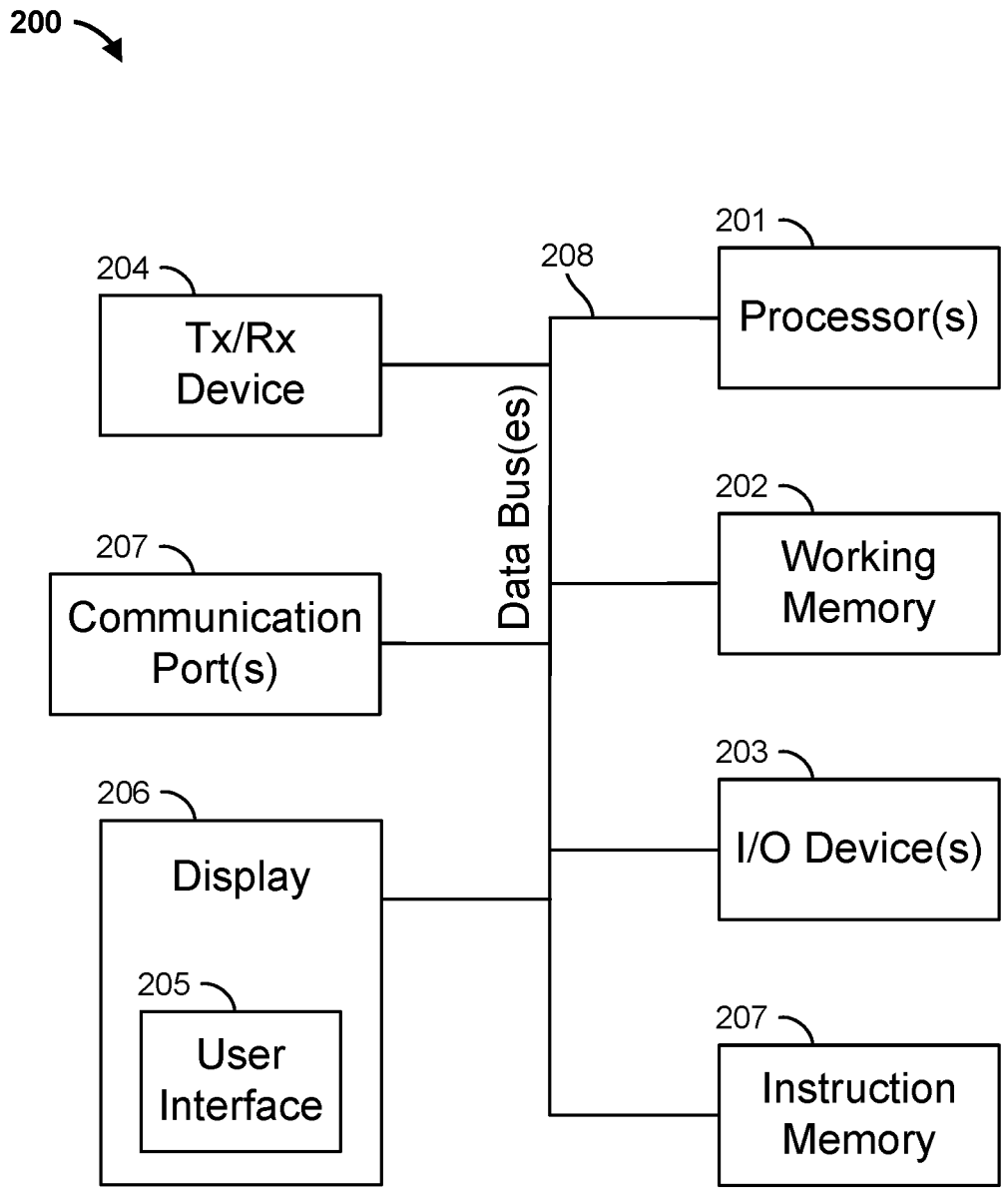
FIG. 2 is a block diagram of the surrogate model computing device of the surrogate model system of FIG. 1 in accordance with some embodiments.

FIG. 2 illustrates an example of a surrogate model computing device 102. Surrogate model computing device 102 includes one or more processors 201, working memory 202, one or more input/output devices 203, instruction memory 207, a transceiver 204, one or more communication ports 207, and a display 206, all operatively coupled to one or more data buses 208. Data buses 208 allow for communication among the various devices. Data buses 208 can include wired, or wireless, communication channels.

Processors 201 can include one or more distinct processors, each having one or more cores. Each of the distinct processors can have the same or different structure. Processors 201 can include one or more central processing units (CPUs), one or more graphics processing units (GPUs), application specific integrated circuits (ASICs), digital signal processors (DSPs), and the like.

Processors 201 can be configured to perform a certain function or operation by executing code, stored on instruction memory 207, embodying the function or operation. For example, processors 201 can be configured to perform one or more of any function, method, or operation disclosed herein.

Instruction memory 207 can store instructions that can be accessed (e.g., read) and executed by processors 201. For example, instruction memory 207 can be a non-transitory, computer-readable storage medium such as a read-only memory, an electrically erasable programmable read-only memory (EEPROM), flash memory, a removable disk, CD-ROM, any non-volatile memory, or any other suitable memory.

Processors 201 can store data to, and read data from, working memory 202. For example, processors 201 can store a working set of instructions to working memory 202, such as instructions loaded from instruction memory 207. Processors 201 can also use working memory 202 to store dynamic data created during the operation of surrogate model computing device 102. Working memory 202 can be a random access memory (RAM) such as a static random access memory (SRAM) or dynamic random access memory (DRAM), or any other suitable memory.

Input-output devices 203 can include any suitable device that allows for data input or output. For example, input-output devices 203 can include one or more of a keyboard, a touchpad, a mouse, a stylus, a touchscreen, a physical button, a speaker, a microphone, or any other suitable input or output device.

Communication port(s) 207 can include, for example, a serial port such as a universal asynchronous receiver/transmitter (UART) connection, a Universal Serial Bus (USB) connection, or any other suitable communication port or connection. In some examples, communication port(s) 207 allows for the programming of executable instructions in instruction memory 207. In some examples, communication port(s) 207 allow for the transfer (e.g., uploading or downloading) of data, such as surrogate model data.

Display 206 can display user interface 205. User interfaces 205 can enable user interaction with surrogate model computing device 102. For example, user interface 205 can be a user interface for an application of a retailer that allows a customer to initiate the return of an item to the retailer. In some examples, a user can interact with user interface 205 by engaging input-output devices 203. In some examples, display 206 can be a touchscreen, where user interface 205 is displayed on the touchscreen.

Transceiver 204 allows for communication with a network, such as communication network 118 of FIG. 1. For example, if communication network 118 is a cellular network, transceiver 204 is configured to allow communications with the cellular network. Processor(s) 201 is operable to receive data from, or send data to, a network, such as communication network 118, via transceiver 204.

Referring back to FIG. 1, each of multiple customer computing devices 112, 114 can be a laptop, a computer, a mobile device such as a cellular phone, a smart phone, a tablet, a personal assistant device, a voice assistant device, a digital assistant, or any other suitable device. Although FIG. 1 illustrates two customer computing devices 112, 114, surrogate model system 100 can include any number of customer computing devices 112, 114. Similarly, surrogate model system 100 can include any number of surrogate model computing devices 102, systems 104, and databases 116.

System 104 can be any system that takes in one or more inputs, and produces one or more outputs. Inputs and outputs may include, for example, data (e.g., signal data, control data, sensor data, specification data), material, fuel, or any other input. System 104 can include any number of subsystems 105 that are operatively or communicatively coupled to each other. For example, a first subsystem 105 of system 104 may receive one or more system inputs, and provide one or more subsystem outputs. A second subsystem 105 of system 104 may receive one or more of the outputs of the first subsystem 105, and provide one or more subsystem outputs. Similarly, system 104 may include additional subsystems. System 104 may provide one or more outputs, such as one or more outputs of any subsystem 105.

Communication network 118 can be a WiFi® network, a cellular network such as a 3GPP® network, a Bluetooth® network, a satellite network, a wireless local area network (LAN), a network utilizing radio-frequency (RF) communication protocols, a Near Field Communication (NFC) network, a wireless Metropolitan Area Network (MAN) connecting multiple wireless LANs, a wide area network (WAN), or any other suitable network. Communication network 118 can provide access to, for example, the Internet.

Surrogate model computing device 102 is operable to communicate with database 116 over communication network 118. For example, surrogate model computing device 102 can store data to, and read data from, database 116. In this example, database 116 may store data identifying and characterizing one or more surrogate models (SMs) 117. Surrogate models 117 may include, for example, an exhaust manifold SM. Surrogate model computing device 102 may obtain and execute a surrogate model 117. Database 116 can be a remote storage device, such as a cloud-based server, a memory device on another application server, a networked computer, or any other suitable remote storage. Although shown remote to surrogate model computing device 102, in some examples, database 116 can be a local storage device, such as a hard drive, a non-volatile memory, or a USB stick.

In some examples, surrogate model computing device 102 may generate one or more surrogate models 117, and store them in database 116. One or more of customer computing devices 112, 114 may access and execute surrogate models 117. Each SM may include an architecture that uses physics or mathematically informed approaches (simplified physics, finite element analysis, chemical processes, etc.) and data-driven statistical approaches (regression, multivariate statistics, Bayesian approaches, Uncertainty Quantification (UQ) methods, etc.) in a multi-stage structure. The SMs can be trained, improved, and validated to optimize predictive capabilities. As a result, computational times required to develop SMs are reduced, and their predictive capabilities are increased. Additionally, the use of physical or mathematically informed approaches in each SM reduces the amount of data required to train the respective SM to achieve the higher predictive accuracies.

A generated SM may predict the output (O) of a system to received inputs ($\bar{x}$). Each output can be, for example, a quantification of the systems present state, past states, or future states. For example, an SM may be generated to predict the remaining useful life of a component in an engine. In this case, the SM may predict present machine states and future machine states of the engine. The output of the SM ($O_{SM}$) may be a prediction of O. Therefore, an error (E) (e.g., a system error) may be defined as $O-O_{SM}$, in other words, the difference between an output O of the system and the predicted output of the system $O_{SM}$. The output of the system O can be identified by, for example, experimental data, field data, IoT data, and/or simulation results.

In some examples, surrogate model computing device 102 generates an SM based on the following steps.

Step 1: Variable Correlations

Surrogate model computing device 102 may start SM development by evaluating correlations between input variables and output variables, correlations between input variables, and correlations between output variables, of a system. Correlations may be computed based on any suitable correlation algorithm, such as a covariance algorithm, Pearson's correlation algorithm, any algorithm expressing a linear or nonlinear relationship between the variables, or any other suitable correlation algorithm. Based on the correlations, surrogate model computing device 102 may generate a correlation matrix [C] that identifies and characterizes the correlations. For example, take 5 input variables $x_1$, $x_2$, $x_3$, $x_4$, $x_5$ that are potential input variables to a system and that may have an influence on outputs $y_1$ and $y_2$. The correlations in this example may be as indicated by correlations C illustrated in the chart below:

|       | $x_1$ | $x_2$      | $x_3$      | $x_4$      | $x_5$      | $y_1$      | $y_2$      |
|-------|-------|------------|------------|------------|------------|------------|------------|
| $x_1$ | 1     | C($x_1$, $x_2$) | C($x_1$, $x_3$) | C($x_1$, $x_4$) | C($x_1$, $x_5$) | C($x_1$, $y_1$) | C($x_1$, $y_2$) |
| $x_2$ |       | 1          | C($x_2$, $x_3$) | C($x_2$, $x_4$) | C($x2$, $x_5$)  | C($x_2$, $y_1$) | C($x_2$, $y_2$) |
| $x_3$ |       |            | 1          | C($x_3$, $x_4$) | C($x_3$, $x_5$) | C($x_3$, $y_1$) | C($x_3$, $y_2$) |
| $x_4$ |       |            |            | 1          | C($x_4$, $x_5$) | C($x_4$, $y_1$) | C($x_4$, $y_2$) |
| $x_5$ |       |            |            |            | 1          | C($x_5$, $y_1$) | C($x_5$, $y_2$) |
| $y_1$ |       |            |            |            |            | 1          | C($y_1$, $y_2$) |
| $y_2$ |       |            |            |            |            | C($y_2$, $y_1$) | 1          |

Here, C(a,b) represents the correlation between variables a and b. The correlation matrix provides initial insight into the relationship between all variables. This information can be used to classify input variables that exhibit high levels of impact to the outputs through, for example, ranking of the input variables based on correlation to output variables. Following the previous example, one example of an input variables rank matrix [R] is illustrated below:

|  | Input Variables | | | | | Outputs | | Rank | |
|---|---|---|---|---|---|---|---|---|---|
|  | $x_1$ | $x_2$ | $x_3$ | $x_4$ | $x_5$ | $y_1$ | $y_2$ | $y_1$ | $y_2$ |
| $x_1$ | 1 | $C(x_1, x_2)$ | $C(x_1, x_3)$ | $C(x_1, x_4)$ | $C(x_1, x_5)$ | $C(x_1, y_1)$ | $C(x_1, y_2)$ | 4 | 1 |
| $x_2$ |  | 1 | $C(x_2, x_3)$ | $C(x_2, x_4)$ | $C(x_2, x_5)$ | $C(x_2, y_1)$ | $C(x_2, y_2)$ | 1 | 3 |
| $x_3$ |  |  | 1 | $C(x_3, x_4)$ | $C(x_3, x_5)$ | $C(x_3, y_1)$ | $C(x_3, y_2)$ | 3 | 2 |
| $x_4$ |  |  |  | 1 | $C(x_4, x_5)$ | $C(x_4, y_1)$ | $C(x_4, y_2)$ | 2 | 4 |
| $x_5$ |  |  |  |  | 1 | $C(x_5, y_1)$ | $C(x_5, y_2)$ | 5 | 5 |
| $y_1$ |  |  |  |  |  | 1 | $C(y_1, y_2)$ |  |  |
| $y_2$ |  |  |  |  |  | $C(y_2, y_1)$ | 1 |  |  |

In the above example, for output $y_1$, correlation $C(x_2,y_1)$ is ranked first. In other words, input $x_2$ is correlated to output $y_1$ more so than any other input x. Similarly, for output $y_2$, correlation $C(x_1,y_2)$ is ranked first. In other words, input $x_1$ is correlated to output $y_2$ more so than any other input x.

Additionally, the input variables with high correlation with each other may indicate that one is a possible determinant of the other (e.g., if the input variables are highly correlated with each other). In this event, surrogate model computing device 102 may determine that only one of the two (or more) of the highly correlated input variables are needed for the SM. The variable to be selected, for example, may be the one with the highest rank in the rank matrix [R]. Highly correlated input variables may also be mathematically combined as one. One example of this is through the execution of a non-dimensionalization algorithm using Buckingham Pi Theorem. In this manner, the number of input variables can be reduced in number, simplifying the SM. In a similar way, the correlation between output variables can be used to reduce the number of output variables, such as by identifying statistical and/or mathematical relationships between them. In the example of two output variables, $y_1$ and $y_2$, that are highly correlated, $y_2=f(y_1)$. These relationships can be linear, exponential, polynomial, power functions, or of any other mathematical relationship. The result of Step 1 is the initial identification and definition of the input vector $\bar{x}$, which may identify a subset of the original input variables in accordance with the above, and output O for the system.

Step 2: Initial SM Creation

Proceeding to the next step, surrogate model computing device 102 may identify one or more principal physical or causal relationships between the input and output variables determined to be most correlated, and/or those variables that have been mathematically combined into one variable, as described above in Step 1, to generate a physics model. Physical relationships may include any generalized or well-established mathematical relationships that associates the inputs and the outputs. The basis of for these relationships can be physical constraint principles, conservation of mass principles, conservation of energy principles, second law of thermodynamics, heat transfer equations, fluid flow equations, materials science equations, mass transfer principles, fluid phase change principles, magnetics principles, gravitation principles (e.g., F=mass*gravity), material behavior, or economic models, physics equations, among others. In some examples, the physical relationships may include a combination of these functions. The goal is to inform and bound the SM to one or more guiding mathematical relationships.

In some examples, weights (e.g., coefficients) are added to the functions and, more specifically, to variables of the functions. The weights may emphasize, or deemphasize, the importance of the variables. In some examples, the weights are predetermined. For example, the weights may be determined based on historical system input and output data. The weights may be stored in database 116 as part of a look-up-table. In some examples, the weights are determined based on one or more machine learning techniques. For example, a machine learning algorithm may be trained with historical system input and output data (e.g., input or output data as represented by a variable of the function) to determine the weights. Once the machine learning algorithm is trained, the provided weights may be applied in the corresponding functions.

As an example, if an SM is created to predict the onset of a crack due to thermomechanical fatigue (TMF), which is induced by changing material temperature in an engine's exhaust manifold, the method would evaluate convective heat transfer, part temperature, and fatigue relations for the material the exhaust manifold is made of. This can be done by using empirical relationships for convective heat transfer and conductive heat transfer to calculate the lumped capacitance temperature of the manifold. Fatigue is caused by the difference in temperatures in the part, and the largest differences have the highest effect. The greatest differences in part temperature will occur during periods and in locations where the exhaust gas flow has changed temperature, causing the wetted part of the exhaust manifold to be close to the gas temperature, while the rest of the part is approximately at the lumped capacitance temperature. This temperature difference can be used to evaluate maximum stress-strain proxy values for the part. From this, fatigue effects can be modeled using conventional strain or stress relationships.

Note that, in this example, the physical problem is over simplified and would not effectively evaluate actual fatigue failure in a complicated shape like an exhaust manifold. However, the method uncovers the right form of the relationship between input and output at this stage and therefore, fitting-coefficients or weights can be added to the physics model that can be adjusted to change key parameters in these physics-based formulas. In the exhaust manifold example, these parameters could be the curvature of the S-N curve, Goodman Stress relationship, the material's Young Modulus, and/or the convective heat transfer relationship. Note that this system of equations is simple and is being calculated based on the transient gas temperature of the exhaust gas passing through the exhaust manifold. The system of equations and the subsequent set of calculations enables optimization of each of the physical phenomena independent of each other.

In some examples, one or more physical relationships may be prescribed and presented to a user, such as an engineer. For example, surrogate model computing device 102 may display the physical relationships in a drop-down menu, or any other selection method, via a software interface displayed on a display. The user may then select the physical relationships (e.g., equations) that govern the problem and select how the input and output variables and assumptions of the equation relate to each other.

In some examples, the physics model generated may not be sufficient to correctly predict the effect of outputs based on input variables for complex systems. In the example of the engine exhaust manifold TMF evaluation, while it is understood that the driver for fatigue is thermal expansion and contraction of the part, the part is in fact three dimensional and has complex fluid flow paths and mechanical features. Moreover, the temperature and flow of the engine exhaust flow has varying temperature, velocity, and convective heat transfer effects in different parts of the exhaust manifold. These complexities are not captured by the simplified physical models developed, even with fitting parameters optimized to reduce the mean square error between SM prediction of thermomechanical fatigue life and actual thermomechanical fatigue of the part.

Step 3: Physics Model Structure Optimization

The extent of simplification or complexity of the physics model may be determined by the acceptability of the error and/or lack of correlation between physics model predictions and a desired SM model output. For example, an oversimplified physics model may not be capturing critical phenomena that determines output. For this purpose, in some examples, surrogate model computing device 102 evaluates the trained physics model for directional correctness and correlation to a desired output (e.g., output O). In some examples, if a correlation (such as one determined as discussed above under Step 1) is less than a predetermined amount (e.g., 0.5), then the physics model may be expanded by capturing further relationships. Examples of expansion of the physics model include, for example, expansion of the dimensionality of the problem by incorporating time and space variables, and incorporation of other physics effects. As the physics model is built in complexity, it is continually evaluated (e.g., calibrated) for correlation to the desired output. Once the physics model achieves the desired threshold of correlation, the physics model structure is finalized. For example, surrogate model computing device 102 may continually evaluate the physics model until the desired threshold of correlation is reached.

Step 4: Physical Model Structure Optimization

To get a better predictive SM, surrogate model computing device 102 may consider and incorporate other input variables not captured by the physics model, including variables in the correlation matrix described above. For example, the initial step of the SM development method discussed above (i.e., Step 1) included evaluating the correlation between input variables and output variables. From this relationship, a subset of input variables can be selected for potential incorporation into the model. They may be incorporated as an adjustment to any portion of the physics model. These adjustments can be in any mathematical form that makes sense for the problem. Thus, for example, $O=f(P(\bar{x}_{physics}), F(\bar{x}_{features}))$, where O is the output function, P is the physics model as a function of the input vector associated with the physics model ($\bar{x}_{physics}$), and F is the feature adjustment function (or feature function) that takes into account additional input variables ($\bar{x}_{features}$). In some examples, $\bar{x}_{features}$ can include input variables not included in the physics model. In some examples, features can include other features of the system. For sake of simplicity, we will refer to these additional variables as feature variables ($\bar{x}_{features}$).

These feature variables can be numerous because they need not necessarily be bound by a physical model. For example, they may include design features, physical constraint features, environmental features, or any feature that affects the functioning of the system. In the example case of the SM for the exhaust manifold TMF described above (and further below), the feature variables can be the numerous design features that describe the geometry of the exhaust manifold. These feature variables may be numerous, such as thousands or even greater. Thus, a reduction in the number of feature variables to identify features that are predictive and significant to the outcome would minimize processing times and costs.

To select an optimum set of features, surrogate model computing device 102 may employ a Modified Stepwise Regression or Genetic Culling algorithm to select an adequate regression model. In this process, the selection of a most accurate or appropriate regression model can be stated as an optimization problem with the objective to select those independent variables that maximize the accuracy of the model according to a statistical criterion. For example, one or more statistical criteria, such as Mean Square Error (MSE), Sum Square Error (SSE), R-Squared, average relative error, or average predictive error may be assessed. In some examples, a Genetic Culling Algorithm may be assessed. One example of the Genetic Culling Algorithm works in the following manner.

First, a features model (F) is developed using all the feature variables. For example if thirty feature variables are being evaluated, then F would be computed using the linear interpolation function $F=\sum_0^{30} w_i x_{features,i}+b$, where $w_i$ is the weight corresponding to the $i^{th}$ component of the $\bar{x}_{features}$ vector, and b is an intercept weight. The weights may be adjusted using any error reduction technique to obtain the optimized form of F using all input variables ($F_0^{30}$ or, more generally, $F_0^N$, where N is the number of feature variables). In these disclosures, the superscript of F denotes the number of feature variables involved in the function, and the subscript of F denotes the iteration of the Genetic Culling process. In some examples, the determination of optimum weights can be based on other error reduction methods that do not involve least square minimization such as, for example, a K-Fold predictive error. Additionally, the form of F does not have to be linear. For example, F can be a neural network, a Kriging function, a polynomial function, or any other mathematical structure that corresponds to the problem.

Once the optimal weights are computed, a new iteration of fitting is conducted. This new iteration eliminates a number of variables, such as one variable, creating a family of possible F functions. Continuing the example, if thirty was the original number of input variables that led to the function $F^{30}$, then the second iteration would lead to thirty new functions $F_1^{29}, F_2^{29}, F_3^{29}, \ldots, F_{30}^{29}$. To assess the predictive capability of each these models, a K-Fold Cross Validation process is used and an average K-Fold error is computed. Only the feature variables that appeared in a top best percentage, such as the best 10%, or a top best number, such as the best three, F functions are retained for further analysis, where the best F functions are those with the lowest K-Fold error.

If all thirty feature variables appear in the best functions, then the feature function with the highest K-Fold error is removed. This process continues until at least one feature variable is eliminated. For example, if the variables in the best three feature functions are retained, in the first iteration of the Genetic Culling process, the variables that appear in the best three feature functions are retained for further analysis in a next iteration. If no variable is eliminated through this selection, then feature variables in the best two feature functions are selected. If, again, this selection does not eliminate at least one feature variable, then the variables in the best feature function is retained for further analysis in the next iteration. In this way, at each iteration, one variable is always eliminated. In other examples, more than one variable is eliminated at each iteration.

The next iteration follows the same procedure as the previous one to eliminate yet another variable and compute a K-Fold Error for each function. As the number of input variables is reduced, the K-Fold Error of the best feature function in each iteration subset changes. The process eliminates variables that over-fit the model, reducing its predictive capacity. The process also identifies high significance variables (e.g., highly significant to the outputs). Surrogate model computing device 102 identifies the (final) input variable set $\bar{x}_{features}$ based on selecting the function $F_m^n$ that has the lowest K-Fold error throughout all iterations.

An alternative Genetic Culling method works in the following manner. Assume there are an N number of feature variables that may have a significant impact on an output, O. As with the previously described Genetic Culling method, the weights (vector $\bar{w}$) are optimized based on minimization of a user defined error or fit criteria. Surrogate model computing device 102 may employ $F_0^N$, a fit function with a particular error, where the superscript denotes the number of feature variables involved in the function and the subscript denotes the iteration of the Genetic Culling process. For predictive SMs, this error is the K-Fold error, which is obtained from K-Fold Cross Validation. As with the previously described Genetic Culling method, a new family of feature functions made up of non-repeating subsets of feature variables that have eliminated at least one of the feature variables is generated. However, surrogate model computing device 102 retains only a subset of these functions for further culling.

For example, assume there are five feature variables, such that N=5. The subsets of feature variables may be as indicated below:

$$\{\bar{x}_1=[x_1,x_2,x_3,x_4], \bar{x}_2=[x_1,x_2,x_3,x_5], \bar{x}_3=[x_1,x_2,x_4,x_5],$$
$$\bar{x}_4=[x_1,x_3,x_4,x_5], \bar{x}_5=[x_2,x_3,x_4,x_5]\}$$

A new set of feature functions is then generated, namely:

$$F_1^{N-1}, F_2^{N-1}, F_3^{N-1}, \ldots, F_m^{N-1}, \ldots, F_N^{N-1}$$

Each one of these function's weights are optimized and the functions are subjected to K-Fold Cross Validation, and an error is measured, as discussed above. A subset of these functions is retained for further variable culling, while the rest is discarded. The number of retained functions can be as high as (N−1) and as low as one. However, in some examples, a top percentage (e.g., 10%) or a top number (e.g., at least 3) of the feature functions that have shown good results are retained. For simplicity, the following description will assume that only the best three feature functions are retained into each next iteration.

Each retained feature function in this first iteration generates N−2 new offspring feature functions with subset feature variables that eliminate a number of variables, such as one, from the previous subset. Assuming one variable is eliminated, the offspring feature functions would be as indicated below:

$$\{F_{1,1}^{N-2}, \ldots, F_{1,m}^{N-2}, \ldots, F_{1,(N-1)}^{N-2}\},$$
$$\{F_{2,1}^{N-2}, \ldots, F_{2,m}^{N-2}, \ldots, F_{2,(N-1)}^{N-2}\},$$
$$\{F_{3,1}^{N-2}, \ldots, F_{2,m}^{N-2}, \ldots, F_{3,(N-1)}^{N-2}\}$$

For each of these feature functions, optimum weights may be computed, and the functions may be subjected to K-Fold Cross Validation. A subset of the best feature functions in this iteration is determined and retained into a next iteration.

Similarly, all further iterations follow the same process until further variable elimination is not possible or practical. For example, iterations may continue up to a maximum number of iterations. In some examples, iterations continue until feature functions remain with a defined number of variables, such as one variable. The best feature function for use in the SM is the one with the lowest error as defined by an error determination algorithm. For predictive analytics problems, the error may be the K-Fold Error (as determined by a K-Fold Error algorithm). In some examples, Surrogate model computing device 102 may perform regression by executing one or more regression analyses algorithms to one or more selected functions to determine whether the fit of a selected function to data is within an acceptable range. For example, an adjusted R-square may be computed based on a selected function to ensure that even though a K-Fold Error for the function is low (e.g., the lowest of all functions), the fit of the selected function to the data is satisfactory.

Step 5: Final Weight Optimization

A final weight optimization is conducted for the final form of the output function O, which includes the physics function (the physics model P) and the feature function (the feature model F). The final weight optimization may be based on one or more machine learning techniques operating on historical system input and output data. Additionally, a final K-Fold Cross Validation error is computed to establish the predictive error of the SM. The final SM may be trained using available data sets, such as data sets identifying system input and output data.

Given the fast computation times, as well as other advantages, of the SMs developed using the embodiments disclosed herein, the SMs have wide-ranging applicability. The following are some of these applications.

Simulation Democratization

Engineering Simulation refers to engineering analysis that simulates the performance of a mechanical, physical, material, electrical, fluid, heat-transfer, or chemical system. Engineering Simulation is typically conducted by experts and, in complex products, the breadth of expertise required can be wide ranging. Additionally, the conduct of Engineering Simulation is time consuming. The combined effect of coordination with experts and computational time slows down product development, as iterations between product design engineers, system engineers, and expert analyst engineers consume time and effort. Additionally, time pressures associated with the product development cycle can lead to conservativism in design, which may hamper innovative thinking and dismiss promising design concepts and solutions.

For classes of products that undergo continuous redesigns, updates and release, the product design history and historical results of Engineering Simulation can act as data sources for the creation of SMs that can predict the most likely result of future simulations for new product designs and use cases. The SMs fast computational speed and simplicity can be transformed into a Designer Tool that does not require expertise for usage. The goal of this type of SM application is to provide Designers with insight as to the likely impact of design decisions. This may increase the quality of the designs, enable fast evaluation of promising new design ideas, and reduce the number of design and Engineering Simulation analysis iterations required to arrive at a final product.

Simulation Validation

SMs can also be developed and used to evaluate Simulation Results in comparison with statistically expected results. Simulation Processes are typically technically complex and, in many cases, require expert abstraction of part physical geometry, the development of meshes that permit accuracy and evaluation efficiency, and inputs of assumptions, initial conditions, and boundary conditions. As a result, Simulation Processes can be error prone. For example in complex analysis, two analysts conducting the same simulation process often arrive at different solutions. In fact, this phenomenon is important to understand. Computational Simulation often provides answers that seem extremely precise. However, this precision is deceptive because changes in mesh size, input conditions, and part abstraction can change results. While a true system result may be unknown, and the result may be bound through statistical evaluation of error, which requires testing & experimentation.

An SM that evaluates the results of Simulation with the predicted results based on historical trends can help analysts determine if an analysis is within an expected precision or not. If not, an error may have been made in the course of conducting the analysis. Further investigation to the unexpected change can lead to important engineering insights and innovations.

Enhanced Analysis

Often, complex simulation problems do not easily lend themselves to design exploration. Large computational requirements and complex relationships between input variables, initial assumptions, meshing methods, and physics being modeled can make design changes or evaluation of new operating conditions extremely expensive and laborious to conduct. Thus, existing solutions may provide results with insight into part performance in a narrow range of conditions. Product designers and analysts may be interested in further design explorations while minimizing the number of simulation runs, for example. The embodiments described herein may alleviate or solve one or more of these issues.

Digital Twins

Digital Twins are models of real products or components that can utilize the data collected from a product to determine the state of the real product and predict its future state based on existing or projected conditions. Digital Twins can be an extremely powerful tool for maximizing product performance, prevent undue product damage, and optimize product lifecycle value. Digital Twin systems based on the SMs disclosed herein may be able to run faster, may require less data storage costs, may require less instrumentation, may reduce data transmission costs, and may enable Edge Computing, for example.

In some examples, a Digital Twin structure is composed of one or more sensors on a system (e.g., product) that transmit data to a processor that at least packages, filters, analyses, or stores said data. The computational simplicity of the SM enables their programming into the processor. In this way, the processor can evaluate the state of the machine and can utilize prior received data to make predictions of prior machine states. The processor can also evaluate changes, provide alerts, or make adjustments to the product's control system such that its operation is enhanced. The processor may also transmit data and the results of the SM through an Internet of Things (IoT) data capture and transmission system.

In one embodiment only the SM results are transmitted. The transmission of SM results, rather than raw data, reduces the amount of data transmitted, which reduces the cost of data transmission and storage for the system. When SM results are transmitted from multiple products, the results of multiple SMs can be compared for various goals such as: optimization of fleet operation; providing recommendations to a user or fleet operator; classify machine use cases based on their state; and/or to verify simulation models, the expected performance of designs, and/or the results of testing. The verification and classification can be done using statistics or data evaluation methods such as T-Testing, evaluation of means, statistical significance analysis, ANOVA analysis, discriminant analysis, Eigen value evaluation, logistic regression, Naive Bayes Classifier, Decision Trees, Vector Machines, Neural Network structures, etc.

Testing

SMs can be used to validate test results with Simulation or Field Data, to verify that test results correspond to expected performance, develop designs of experiment that reduce the amount of experimental runs required, and/or to develop accelerated testing techniques. Through the Multi-Step SM development method described above, the final form of an SM is made up of a physics model and a features model. The analysis of impact of variables to test results that comes from the SM development process and from the final form of the SM itself can be used to identify the key variables that should be changed, and to what magnitude (e.g., by adding or adjusting weights), during a test. This may reduce the number of factors that are needed for performance validating tests, which reduces testing time and costs.

Additionally, SMs can adapt testing conditions to accelerate the onset of a result. For example, product or part failure may be difficult to test because most products are designed for multi-year operation. An alternative is to use an SM to identify testing parameters that would result in part failure over a reasonable period of time (e.g., over a portion of an expected life expectancy of the part). By comparing SM results to actual results, the predictive capability of the SM may be verified. If the SM is accurate in its prediction of the accelerated result, it can be deemed to be predictive of the actual part life under non-accelerated test conditions.

In some instances the SMs can be used to evaluate the quality of data received from sensors in a machine. Sensor data that relate to machine performance or state, and sensors that provide data on processes or features that affect machine performance or state, are typically used in machine testing and evaluation. The accuracy of these sensors can be affected by multiple factors during machine testing. These factors could include voltage fluctuations, temperature excursions, temperature changes, humidity, vibration, shock, bad placement, and damage, among other things. Given the expense of tests, it is useful to have real time evaluation of the quality of the data provided by sensors. For this, a SM in accordance with the embodiments herein may be used. The SM predicts the machine's performance and/or state based on data received by the sensors. If the SM prediction varies substantially from the machine's actual performance, then this may be an indication of sensor error. The SM may also be trained to relate bounds of probable or acceptable sensor readings (e.g., sensor range readings) based on the data of other sensors in the machine. If the relationships between machine sensors is outside statistically probable relationships, then there is a high likelihood that a sensor error exists.

An alternative application to these methods is the use of the SM to adapt machine controls to the loss of a sensor. In this case, the SM can predict the most likely output of a damaged sensor, and this prediction may be provided as an input to the machine's control system. Through this method, the life of the machine can be extended. This may be particularly important for machines that are difficult to service or that must maintain operation even when certain sensors are no longer operational.

Figure 8:
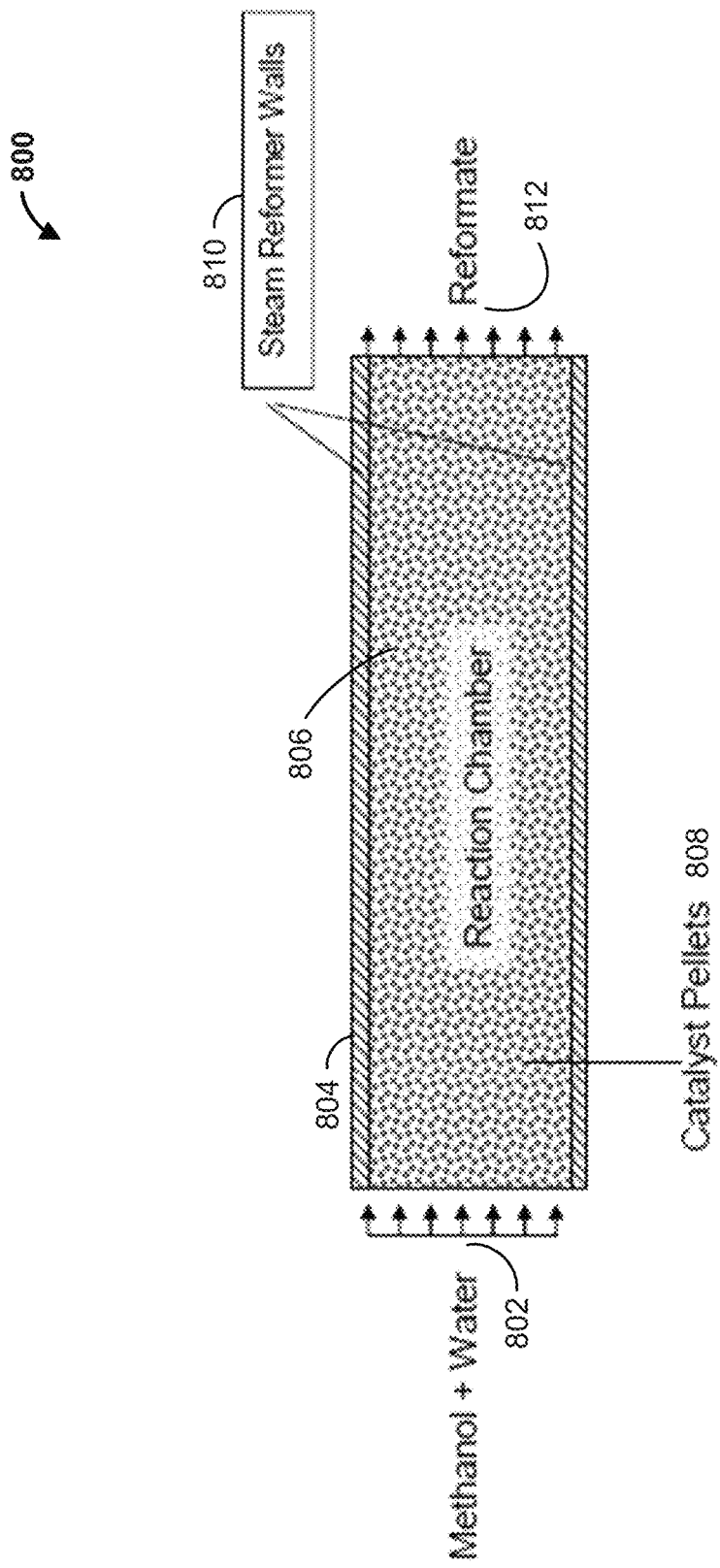
FIG. 8 illustrates an example use case for the surrogate model of FIG. 1 in accordance with some examples.

FIG. 8 illustrates an example use case for the surrogate model of FIG. 1 for a methanol steam reformer 800. The methanol reformer 800 design is a cylinder tube 804 with incoming vaporized methanol water mix 802 entering the cylinder tube 804 at one end. A reaction chamber 806 of the tube 804 is filled with reformation catalyst 808 in a packed bed arrangement. The cylinder tube 804 is surrounded by flowing combustion gases that flow on the exterior of the cylinder tube 804. These combustion gases are hot and transfer heat to the cylinder tube 804 and its contents. The catalyst 808 promotes the steam reforming reaction of methanol ($CH_3OH$) and water ($H_2O$) into hydrogen ($H_2$), carbon dioxide, ($CO_2$), and carbon monoxide (CO). The idealized reaction is: $CH_3OH + H_2O \rightarrow 3H_2 + CO_2$. Designers have multiple design features that may affect the performance of the methanol steam reformer. An analysis of correlations and ranking include the following features: length of cylinder tube, inner diameter of cylinder tube, temperature of the combustion gases, mass flow rate of methanol water mix, temperature of methanol water mix, catalyst packing density, and material of the cylinder tube.

The desired output 812 of the steam reformer 800 is to generate reformate that has maximum conversion of methanol to maximize methanol conversion to hydrogen and have the minimum concentration of carbon monoxide in the output. Additionally, the reformer 800 is bound by constraints that would affect life of the part. In particular, catalyst damage can occur at elevated temperatures (>900° C.). Catalyst 808 damage leads to decreased reaction rates in time and eventual loss of reformation capacity of the system. The steam reforming reaction of methanol is endothermic. The rate of reaction of methanol is dependent on temperature. Higher temperatures promote faster reactions rates. Additionally, reaction rate of reaction is affected by the concentration of the reactants. Given this, the hydrogen concentration leaving the steam reformer will be governed by coupled relationships between heat transfer within the catalyst bed, chemical kinetics of the steam reforming reaction, and fluid dynamics. If a finite element modeling process were to be used to solve for hydrogen concentration for a given design of the steam reforming, the usual process would first evaluate packaging density based on probabilistic placement and flow of catalyst pellets into the cylinder tube; then a computational fluid dynamic (CFD) model coupled with heat transfer and reaction kinetics models would be run. This finite element analysis process could take days to complete, given standard computational systems.

For SM development the heat transfer and heat balance equation is the following:

$$\rho_{eff} C_{eff} \frac{\partial T}{\partial t} = \frac{k_{eff}}{r} \frac{\partial T}{\partial r} + k_{eff} \frac{\partial^2 T}{\partial r^2} + k_{eff} \frac{\partial^2 T}{\partial x^2} - \frac{d\dot{E}_g}{dV} + u\rho_{gas}(1-\varepsilon) C_{p,gas} \frac{\partial T}{\partial x}, \text{ where } \rho_{eff}$$

is the effective mass density of the catalyst-gas mixture, $C_{eff}$ is the effective specific heat of the catalyst-gas mixture, T is the temperature inside the cylindrical tube, $k_{eff}$ is the catalyst-mixture effective thermal conductivity, r is the radial coordinate of the cylinder tube, x is the axial coordinate of the cylinder tube, $\dot{E}_g$ is the net rate of heat absorbed by the steam reforming reaction, V is the reformer volume, $\rho_{gas}$ is the density of the gas, $\varepsilon$ is the void factor of packed bed catalyst, and $C_{p,gas}$ is the average specific heat of the gas. For simplicity, it can be assumed that the thermal capacitance of the mass inside the control volume is primarily due to the presence of the catalyst. Therefore $\rho_{eff} C_{eff}$ is approximately equal to the catalyst density ($\rho_c$) multiplied by the catalyst's specific heat ($C_c$) and the void factor ($\varepsilon$). For simplicity, the axial convective heat transfer term, $$\left( u\rho_{gas}(1-\varepsilon) C_{p,gas} \frac{\partial T}{\partial x} \right),$$

is neglected for SM purposes. $\dot{E}_g$ is a function of the rate in which methanol is reacted in the steam reforming reaction $$\frac{d[CH_3OH]}{dt}.$$

This in turn is a function of temperature (T), catalyst volume ($dV_c$), and the molar concentration of methanol in the reformate gas ($x_{MeOH}$). The rate of methanol reacted per unit mass of catalyst ($r_M$) follows the Arrhenius relationship developed by Nakagaki et al:

$$r_M = kP^l \left( \frac{T}{513} \right)^m e^{\frac{-E}{RT}} x_{MeOH}^n.$$

For Nagakaki, this empirical relationship had k value of $1.35 \cdot 10^6$ mol/($g_{cat}$ s atm); the value of m is −10 if T is greater than 513K or else its 0; the value of E is $1 \cdot 10^5$ J/mol; the value of l is 0.13, and the value of n is 1.3. The coupled chemical equation and heat transfer equation is thus:

$$\rho_c \varepsilon C_c \frac{\partial T}{\partial t} = \frac{k_{eff}}{r} \frac{\partial T}{\partial r} + k_{eff} \frac{\partial^2 T}{\partial r^2} + k_{eff} \frac{\partial^2 T}{\partial x^2} - \varepsilon \rho_c E_r r_M,$$

where $E_r$ is the energy consumption of the methanol steam reforming reaction. The above governing equation is used to reduce the number of variables that determine reformer performance based on an understanding of the underlying physics of the problem. To do this, the equation can be non-dimensionalized. For this we define the maximum potential reformation capacity of a reformer tube. This value is assigned the symbol Ω. This is defined as the theoretical hydrogen power ($P_{H2}$) that a certain mass of catalyst could produce if the steam reformer cylindrical tube was maintained at exactly the wall temperature ($T_w$), and with the methanol concentration at the inlet of the reformer cylinder tube. This can be calculated using the Nagakaki relationship. Additionally, a non-dimensional temperature θ is defined as equal to $$\frac{T}{T_w}.$$

Similarly, a non-dimensional length and radius can be defined as $$r^* = \frac{r}{R} \text{ and } x^* = \frac{x}{L}.$$

Given these definitions the governing equation can be written in the following non-dimensional form:

$$\frac{V\rho_c \varepsilon C_c T_w}{\Omega} \frac{\partial \theta}{\partial t} =$$

$$\frac{V T_w k_{eff}}{R^2 \Omega} \frac{1}{r^*} \frac{\partial \theta}{\partial r^*} + \frac{V T_w k_{eff}}{R^2 \Omega} \frac{\partial^2 \theta}{\partial r^{*2}} + \frac{\pi R^2 T_w}{V\Omega} \frac{\partial^2 \theta}{\partial x^{*2}} - \frac{\varepsilon \rho_c E_r r_M V}{\Omega}.$$

This equation derives important non-dimensional terms that have impact on reformer performance. These are non-dimensional conduction, $$k^* = \frac{V T_w k_{eff}}{R^2 \Omega}$$

and the time constant, $$\tau = \frac{V\rho_c \varepsilon C_c T_w}{\Omega} = \frac{C_c T_w}{3 LHV_{H2} r_{M,max}}.$$

Additionally, a catalyst effectiveness, $$= \frac{\varepsilon \rho_c E_r r_M V}{\Omega}.$$

Reformers with the same non-dimensional conduction and time constant should have similar performance. In this example, the most important reformer characteristic is its efficiency (ref) defined as the power of hydrogen delivered by reformer divided by the power of fuel introduced into the reformer. Also, the flow of methanol into the steam reformer can be non-dimensionalized using the continuity equation to be:

$$\frac{1}{\eta_{ref,max}} \left( \frac{n_{MeOH,in}}{n_{MeOH,reacted,max}} \right) \text{ where }$$

-continued $$\eta_{ref,max} = \frac{3 LHV_{H2}}{LHV_{MeOH}}, n_{MeOH,in}$$

is the molar rate of methanol entering the reformer cylinder, $n_{MeOH,reacted,max}$ is the theoretical maximum molar amount of methanol that the reformer could react.

Other features affect the reformer efficiency that are not part of the simplified physical structures discussed. In particular, the wall temperature is not constant and is dependent on the reformer burner design, small changes in catalyst formulations that modify the Nagakaki relation, variations in methanol water mix at the reformer entry region based on nozzle design, etc. These and other design variables make up the feature variable vector $x_{features}$. The SM for the steam reformer efficiency takes the form: $\eta_{SM}=P(k^*,\lambda,\tau,flow_{ND})+F(x_{features})$, where P is the physics function and F is the features function. The form of P is: $P=[Ak^{*a}+B\lambda^b+Cflow_{ND}^c]e^{-g\tau t}$, where A, B, C, a, b, c, and g, are weights for fitting the model to data. Additionally, a weight ($w_r$) may be added to the rate of reaction formula such that $$r_M = w_r k P \left(\frac{T}{513}\right)^m e^{\frac{-E}{RT}} x_{MeOH}^n.$$

The features has the following structure, $F=\Sigma_i w_i x_i$.

Given this formulation the weights of P are fitted using data derived from testing of reformer tubes based on a 3 sample full factorial design (64 points). Note that the reduced number of data required is due to the non-dimensionalization of the underlying physics. The training in this example is done by minimizing least square error between model prediction and data output. The model's predictive capabilities was evaluated using 5-fold K-Fold cross validation. This yields a first iteration of an optimized P function. The same experimental data may be used to evaluate F, but in this case, a Genetic Culling algorithm is employed to reduce the components of the x vector by evaluating the form of F that yields the lowest predictive error based on K-Fold cross validation analysis. The final form of the SM is arrived at through a final re-training of the "culled" F function and of the P function based on minimization of K-Fold predictive error.

The SM may be implemented in a controller microchip that evaluates input variables and features to predict the reformer efficiency. This allows, for example, for improved controls and operational optimization of the reformer, and may be coupled with other SM models that govern the behavior of downstream processes. One such optimization is the control of the reformer burner, which has influence on $T_w$ and thus dictates the values of both $k^*$ and τ. Additionally, $T_w$ is related to catalyst sintering. Through the use of the SM, $T_w$ may be inferred from reformer efficiency data, thereby eliminating the need for certain sensors or providing an evaluation of sensor damage through comparison to the SM calculated $T_w$.

SM Generation for Evaluating Thermomechanical Fatigue (TMF) in an Exhaust Manifold System In one example, an SM may be generated to evaluate thermomechanical fatigue (TMF) in an exhaust manifold system, such as the exhaust manifold of an engine. The exhaust manifold of an engine is subject to varying flows of hot engine exhaust when the engine is in operation. This variation in temperature and flow rate generates transient temperature gradients that create stress and strain within the exhaust manifold. In time, these varying stresses and strains can cause a crack to form and propagate in the exhaust manifold, which can eventually lead to loss of performance and failure. The SM can simulate the TMF process experienced by the exhaust manifold. The SM may simulate, for example, cycles of exhaust gas flow and temperatures that may be experienced by the exhaust manifold.

The SM may generate simulation results that can be used to determine whether system requirements, such as useful life and maximum conditions, can be met. The simulation results can also be used to verify that the design of the exhaust manifold is adequate for its intended purposes.

The SM is developed based on simulation data derived from actual exhaust manifold systems, and employs finite element methods to predict the results of exhaust manifold TMF. For example, the SM is trained with a plurality of simulation runs with varying exhaust manifold designs. Development of the SM also includes initial correlation analysis to reduce the number of variables (input or output variables) that depict the physical geometry, design, or composition of exhaust manifolds.

To develop the SM, a physics model is developed. The physics model can be defined as $P = f(\overline{w}_{physics}, \overline{x}_{physics})$, where $\overline{w}_{physics}$ is a vector of weight values used to calibrate the P and $\overline{x}_{physics}$ is a vector of values for the independent variables for P.

The physics model can use cycling transient gas temperature ($T_g$) and flow rates and converts them into a convective heat transfer model using Nusselt Number standard correlations for pulsating flow. From this the convective coefficient, h, can be determined. The convective heat transfer coefficient and gas temperature is used to develop a lumped capacitance temperature ($T_P$) for the exhaust manifold based transient heat balance. A radiation heat transfer term, $\varepsilon\sigma(T_P^4 - T_{sur}^4)$, can also be determined by allowing the exhaust manifold to cool down by the environment's temperature ($T_{sur}$). The radiation heat transfer term has been determined to improve consistency with average part temperatures obtained from simulation data. The following is an example of a lumped capacitance equation determined in accordance with the development of the physics model:

$$\frac{dT_P}{dt} = \frac{-1}{\rho Vc}[SA \cdot h(T_P - T_{gas}) + SA \cdot \varepsilon\sigma(T_P^4 - T_{sur}^4)].$$

In the equation above, SA is the internal exhaust gas wetted surface area of the exhaust manifold, V is the volume of the exhaust manifold, c is the heat capacity of the material, t is time, and εσ represents a multiplication of the Stefan-Boltzmann constant (σ) and the exhaust manifold's emissivity (ε).

Recognizing that the thermomechanical fatigue life can be driven by differences in exhaust manifold temperatures (e.g., maximum differences in exhaust manifold temperatures, which in turn cause the highest stresses), the gas temperature ($T_g$) minus the lumped capacitance temperature ($T_P$) is used as an input variable to a physics model that can be used to define thermal stresses. Thus, for example, $T_g - T_P$ is directly proportional to the change in stress in the part ($\Delta\sigma$).

A fatigue stress model can be defined according to the following equation:

$$\frac{\Delta\sigma}{2} = \sigma'_f \cdot (2N_f)^b.$$

In the equation above, a is the change in part stress or stress amplitude, $\sigma'_f$ is the endurance stress for a material (e.g., material the exhaust manifold is made of), $N_f$ is the number of cycles of the stress amplitude until the onset of a failure, and b is the Basquin Slope (e.g., as derived from an S-N curve). The equation allows for the determination of what number of cycles a particular amount of stress change would generate part failure. A mean stress adjustment can also be applied, resulting in the following equation:

$$\frac{\Delta\sigma_{adj}}{2} = \frac{\Delta\sigma}{2} \cdot \left[\frac{\sigma_u}{\sigma_u - \overline{\sigma}}\right].$$

In the equation above $\Delta\sigma_{adj}$ is the adjusted stress amplitude, $\sigma_u$ is a material property, and $\overline{\sigma}$ is the mean stress (e.g., a means stress observed by a simulated exhaust manifold). The physics model employs b, $\sigma_u$, $\sigma'_f$, and h as parameters (e.g., fit parameter or adjustable weights), which are optimized to fit the model. These terms may be included as components of a $\overline{w}_{physics}$ vector, such as the $\overline{w}_{physics}$ vector discussed above. The initial conditions for these parameters can be derived from engineering literature, for example. In some examples, the mean stress adjustment can be determined based on other methods as well, such as Gerber, Soderberg, or Morrow algorithms (e.g., formulas).

Stress inversions experienced by an exhaust manifold can affect life expectancy, which can be described using S-N curves, i.e., Woehler curves showing cyclic stress (S) against a logarithmic scale of cycles to failure (N). Given that the cycles of gas temperatures and gas flows through an exhaust manifold are transient and can vary, the part life calculation can employ rainflow counting in addition to accumulation of part damage as a way to evaluate final exhaust manifold life.

To adapt the physics model to predict engineering simulation data, simulation results with varying transient gas temperatures, flow rate cycles, and mechanical designs are used to optimize $\overline{w}_{physics}$ such that the predictive error, measured using K-Fold Cross Validation is minimized. Other optimization techniques, such as minimization of square error, can also be used.

Having developed the physics model (e.g., physics model P), the SM model can be generated. The SM model can be generated in accordance with the following equation: $O = f(P, F)$. Here, P is the physics model, and F is a part features model adjustment. The features model adjustment enables the SM to predict the effects that the design and shape of an exhaust manifold have on TMF life. For example, flow path diameters, blockages to flow, exhaust manifold turns, component proximity to each other, as well as other features, can impact exhaust manifold part temperature changes and stress concentrations.

For TMF, the lumped capacitance temperature (e.g., $T_{p, max}$) of the exhaust manifold associated with each rainflow counted stress amplitude is determined so that the loss of life and damage accumulation on the part can be determined. For the thermomechanical fatigue problem, the principal driver of fatigue failure can be stress amplitude, represented as $\Delta\sigma_{adj}$. Thus, a final form of the SM O can be generated in accordance with the equation below:

$$O = \frac{[\Delta\sigma_{adj} + F(\overline{w}_{features}, \overline{x}_{features})]}{2} = \sigma'_f(2N_f)^b.$$

An alternative method would be to adjust the physics model P after the rainflow count based analysis of life, $N_f$, is determined. This is one of the benefits of the disclosed multi-stage surrogate modeling. In other words, feature correction can be used to adjust any part of the physics model to improve fit and/or predictive capabilities of an SM.

In some examples, the Genetic Culling method is employed to determine an optimum form of F that provides the minimum predictive error for O.

Other physics model could be used for the creation of thermomechanical fatigue SMs. For example, the prediction of fatigue life can be developed using strain-life relationships in accordance with either of the equations below:

$$\frac{\Delta\varepsilon}{2} = \frac{\sigma'_f}{E} \cdot (2N_f)^b + \varepsilon'_f \cdot (2N_f)^c;$$

$$\sqrt{\Delta\varepsilon\Delta\sigma E} = 2\sqrt{(\sigma'_f)^2(2N_f)^{2b} + \varepsilon'_f\sigma'_f E(2N_f)^{b+c}}.$$

Figure 3:
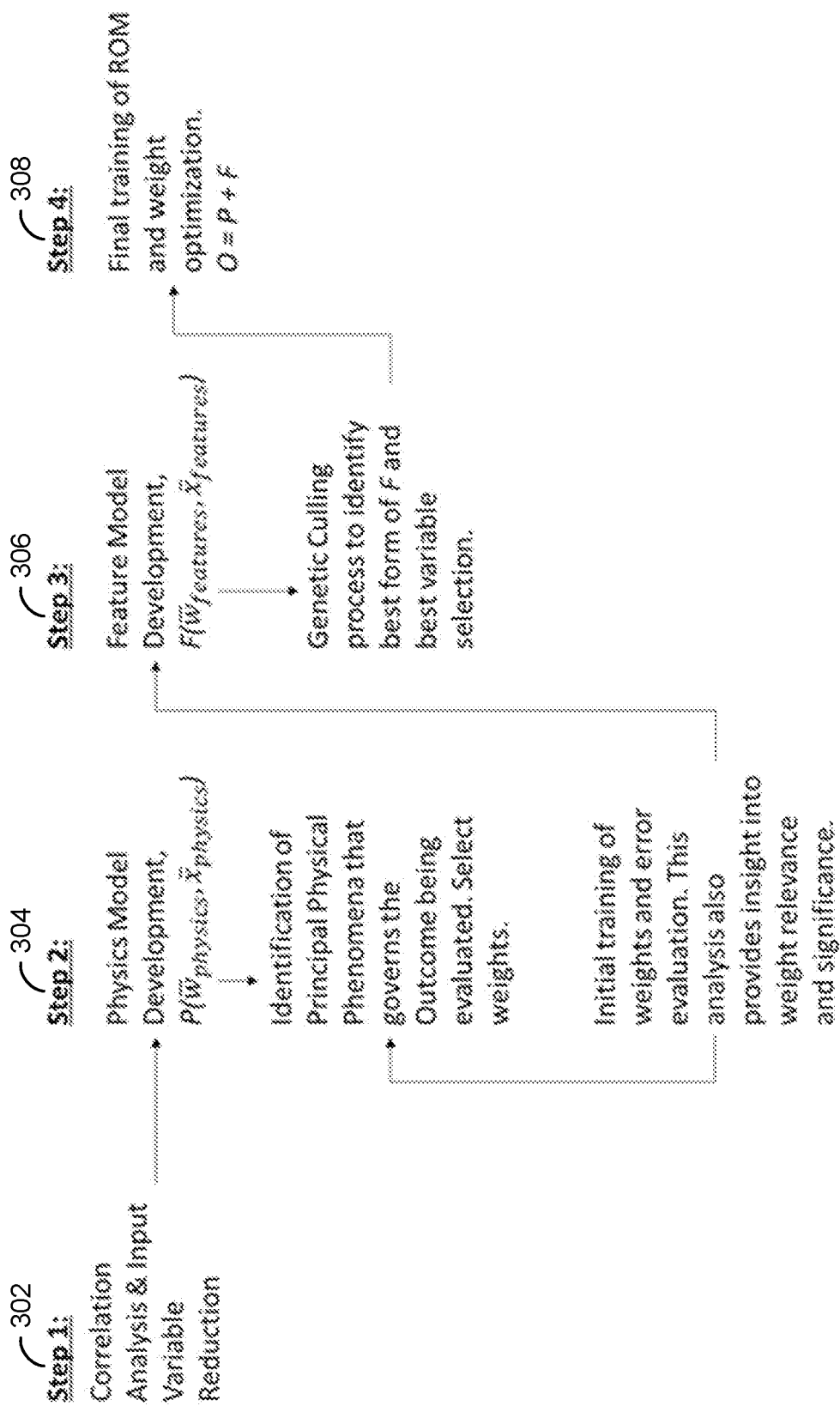
FIG. 3 illustrates a surrogate model development process that may be carried out by the surrogate model system of FIG. 1 in accordance with some embodiments.

FIG. 3 illustrates an SM development process that may be carried out by the surrogate model system of FIG. 1. The SM development process may be one to develop a SM for an exhaust manifold system, for example. At first step 302, correlation analysis between input and output variables is performed. Based on the correlation analysis, the number of input variables may be reduced. For example, in some embodiments, only the input variables most highly correlated to the output variables may be kept for the model. At second step 304, a physics model P is developed based on $\overline{x}_{physics}$ input variables. An original physics model is first identified based on the system or subsystem being modelled. Then, $\overline{w}_{physics}$ weights may be determined and added to generate the physics model P. The selection of weights may be modified based on machine learning training of the physical model.

Third step 306 includes development of a feature model F, which is based on other types of inputs $\overline{x}_{features}$ and determined weights $\overline{w}_{features}$. A genetic culling process is executed to determine a best feature model F, along with required inputs $\overline{x}_{features}$ and weights $\overline{w}_{features}$. The training of weights and error evaluations performed at second step 304 may assist in determining an original feature model F, which is then culled. At fourth step 308, the SM is generated based on the physics model and the feature model. For example, an output O of a system may be characterized as the physics model P plus the best feature model F. In addition, weights for the physics model and the feature model may be optimized at this step as well. The developed SM may be a reduced order model (ROM), for example.

Figure 4:
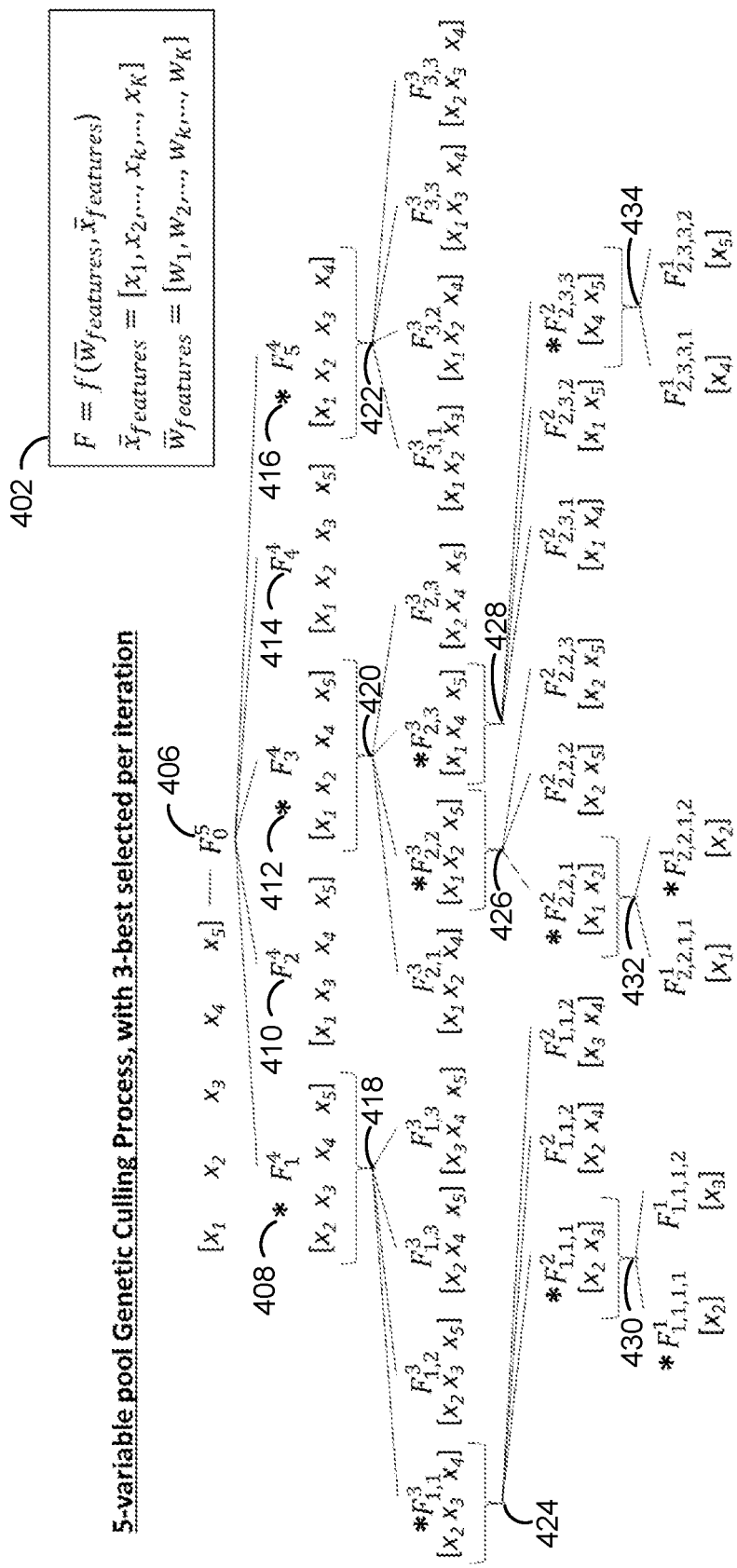
FIG. 4 illustrates a graphical representation of a culling process that may be carried out by the surrogate model system of FIG. 1 in accordance with some embodiments.

FIG. 4 illustrates a graphical representation of a five variable genetic culling process, with the three best functions are selected at each iteration. Although in this example three functions are selected at each iteration, in other examples another number of functions (e.g., 1, 2, 5, etc.) can be selected at each iteration. As illustrated by key 402, a feature model F may be a function $f$ of inputs $\overline{x}_{features}$ and weights $\overline{w}_{features}$. In this example, the original feature model 406 is identified as $F_0^5$ that is based on five inputs $x_1$, $x_2$, $x_3$, $x_4$, and $x_5$. At a first iteration, from original feature model 406 five feature models are generated, each one with fewer inputs (e.g., one less input) than the original feature model 406. For example, each of feature model 408, identified as $F_1^4$, feature model 410, identified as $F_2^4$, feature model 412, identified as $F_3^4$, feature model 414, identifies as $F_4^4$, and feature model 416, identified as $F_5^4$, each are based on four of the five inputs of original feature model 406. In addition, none of these models include the same set of inputs. Based on the execution of a K-Fold Error algorithm, the top three feature models are determined.

This example assumes that feature model 408, feature model 412, and feature model 416 end up with the three most predictive evaluation scores. As such, each of these three feature models are further evaluated. For each of these feature models, an input variable is removed, and four additional feature models are generated. At this iteration, each feature model is based on three variables. For example, feature models 418 are based on feature model 408, each with fewer input variables than feature model 408. Similarly, feature models 420 are based on feature model 412, each with fewer input variables than feature model 412. Feature models 422 are based on feature model 416, each with fewer input variables than feature model 416.

At this iteration, based on the execution of a K-Fold Error algorithm, the top three feature models are determined. Assume that at this iteration feature models $F_{1,1}^3$, $F_{2,2}^3$, and $F_{2,3}^3$ are the top three feature models of this iteration based on the execution of a K-Fold Error algorithm. For each of these feature models, an additional three feature models are generated, but with one less input variable. Specifically, feature models 424, feature models 426, and feature models 428 are based, respectively, on feature models $F_{1,1}^3$, $F_{2,2}^3$, and $F_{2,3}^3$, and each are based on two input variables.

Assuming that, at this iteration, feature models $F_{1,1,1}^2$, $F_{2,2,1}^2$, and $F_{2,3,3}^2$ are the top three models of this iteration based on the execution of a K-Fold Error algorithm, feature models 430, feature model 432, and feature models 434 are generated, respectively, to begin the next iteration. At this iteration, each feature model is based on just one input variable. Here, again, the top three feature models of this iteration are determined based on the execution of a K-Fold Error algorithm.

In some examples, the feature model with the most predictive evaluation score out of multiple (e.g., three) feature models selected at each iteration is selected as the final feature model F to be used for the SM.

For example, in the above example, the final feature model is based on one input variable. However, the final feature model can be based on more than one input variable. For example, in the above described iterative process, once the error (e.g., based on the K-Fold Error algorithm) begins to increase after a variable is eliminated, the iterative process may be stopped and the final feature model may be selected from the remaining feature models. As an example, assume the iterative process has proceeded until there are feature models with only three input variables. For each of these feature models, additional feature models are generated, but with only two input variables. To determine the top feature models of those based on just two input variables, the K-Fold algorithm is executed. If the errors computed for these feature models based on just two input variables is more than the errors computed for the feature models based on three input variables, the final feature model is selected from the feature models based on three input variables.

Figure 5:
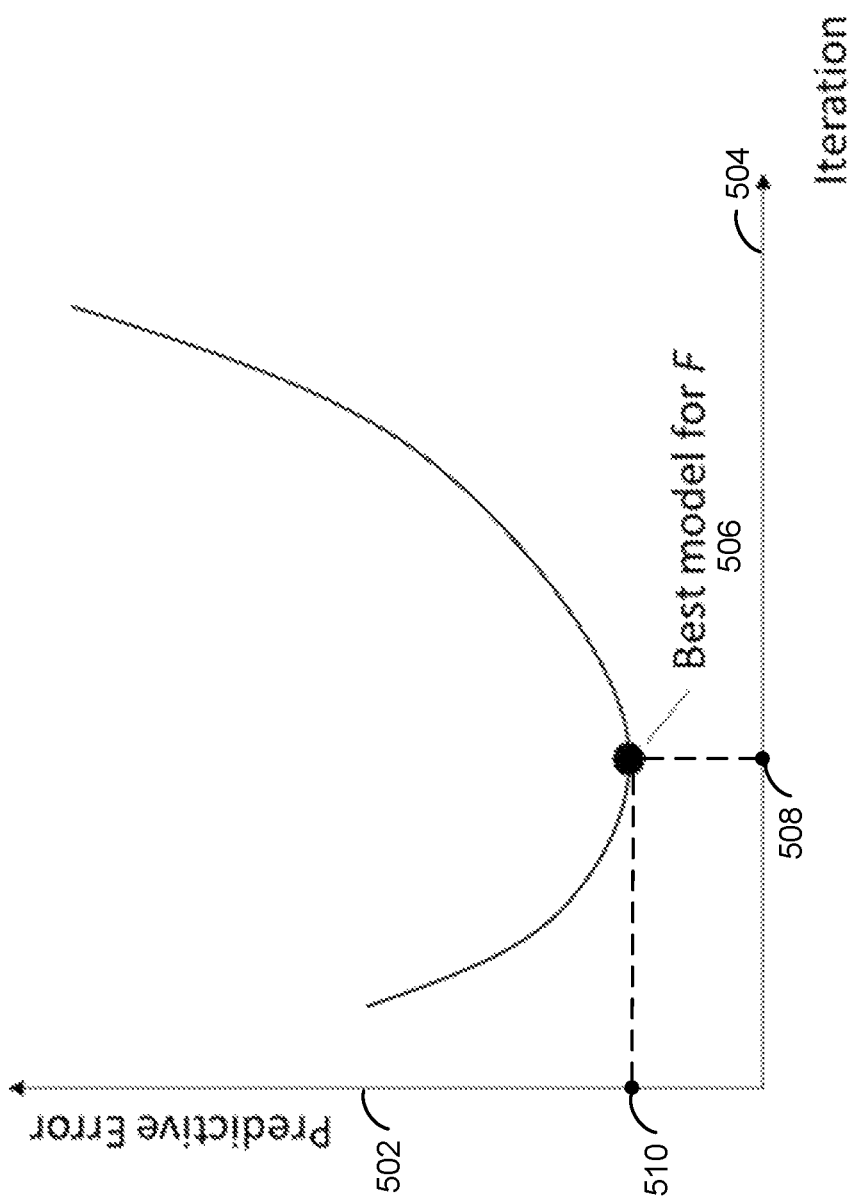
FIG. 5 illustrates a graphical illustration of error reduction that may be realized by the culling process of FIG. 4 in accordance with some embodiments.

FIG. 5 illustrates a graphical representation of error reduction as a function of a genetic culling algorithm iteration. In this example, the y-axis 502 identifies predictive error, and the x-axis 504 identifies the iteration. The best model choice for feature model F is the point 506 where the predictive error is smallest. Specifically, in this example, point 506 identifies the minimum predictive error 510 at iteration 508.

Figure 6:
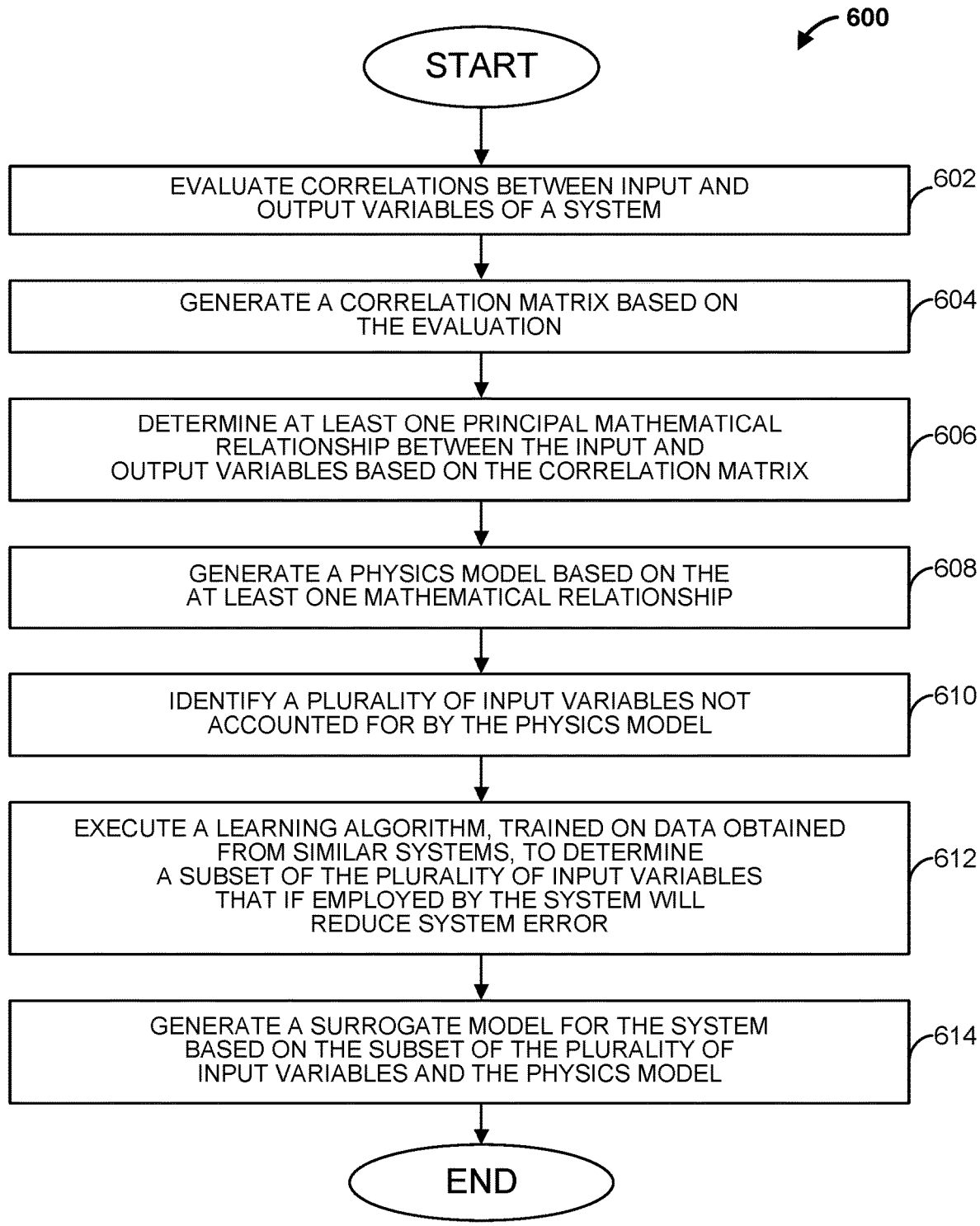
FIG. 6 is a flowchart of an example method that can be carried out by the surrogate model system of FIG. 1 in accordance with some embodiments.

FIG. 6 is a flowchart of an example method 600 that can be carried out by the surrogate model computing system of FIG. 1. Beginning at step 602, correlations between input and output variables of a system, such as an exhaust manifold, are evaluated. At step 604, a correlation matrix is generated based on the correlation evaluations. At step 606, at least one principal mathematical relationship between the input and output variables is determined based on the correlation matrix. For example, a principal mathematical relationship between the most highly correlated input and output variables (e.g., of the exhaust manifold system) may be determined.

Proceeding to step 608, a physics model is generated based on the at least one principal mathematical relationship. The physics model may be a function based on input variables, and weight applied to the input variables. At step 610, a plurality of input variables are identified. The plurality of input variables include variables not identified by the physics model. The plurality of input variables may correlate to system data, environmental conditions, system dimensions, system properties, or any other data that may affect system function or performance. In some examples, at least some of the plurality of input variables are determined based on machine learning techniques.

Proceeding to step 612, a learning algorithm, such as a machine learning algorithm, is executed to determine a subset of the plurality of input variables that best predict system behavior. For example, the subset of the plurality of input variables may be the least number of variables required to predict system behavior to a predetermined degree of certainty. The machine learning algorithm may have been trained on historical system data, such as system data obtained from similar systems in the field. At step 614, a surrogate model (SM) for the system is generated based on the subset of the plurality of input variables and the physics model. The method then ends.

Figure 7:
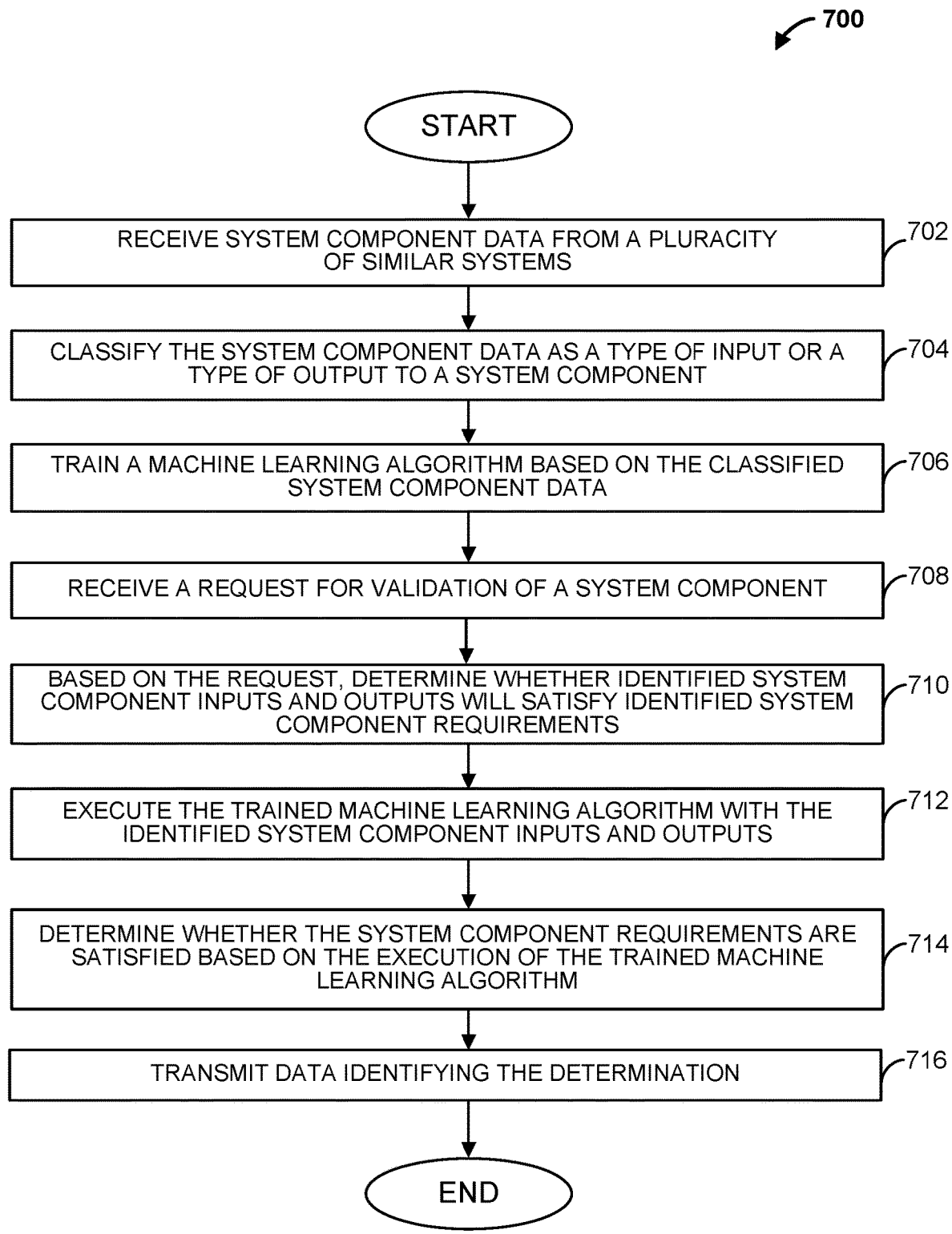
FIG. 7 is a flowchart of another example method that can be carried out by the surrogate model system 100 of FIG. 1 in accordance with some embodiments.

FIG. 7 is a flowchart of another example method 700 that can be carried out by the surrogate model computing system 100 of FIG. 1. Beginning at step 702, system data, such as exhaust manifold system data, is received from a plurality of similar systems (e.g., similar exhaust manifold systems). The system data may be input data, output data, or sensor data, for example. At step 704, the system data is classified as a type of input to or a type of output from the system. At step 706, a machine learning algorithm is trained based on the classified system data.

Proceeding to step 708, a request for validation of the system is received. The request may be received from a customer computing device 112, 114, for example. The request may identify system inputs, system outputs, and system requirements. System requirements can include any system requirement, such as system output requirements, system operating requirements, system power usage requirements, system component estimated life requirements, or any other requirement. For example, exhaust manifold system requirements can include any exhaust manifold system requirement, such as exhaust manifold system output requirements, exhaust manifold system operating requirements (maximum or average temperature, maximum or average pressure, etc.), exhaust manifold system power usage requirements, exhaust manifold system estimated life requirements, or any other requirement. At step 710, the trained machine learning algorithm is executed based on the system inputs and outputs.

At step 712, a determination is made as to whether the system requirements are satisfied based on the execution of the trained machine learning algorithm. For example, a determination may be made as to whether the system outputs are possible given the system inputs and system requirements. At step 714, data identifying whether the system requirements are satisfied is transmitted. For example, surrogate model computing device 102 may transmit the data to another computing device, such as one or more of customer computing devices 112, 114. The method then ends.

In some embodiments, a computing device is configured to identify a mathematical representation of a system, and determine correlations between system input data and system output data of the system. The computing device is also configured to identify at least a portion of the system input data based on the correlations. Further, the computing device is configured to generate a first feature function with function input data based on the identified portion of the system input data, wherein the original feature function characterizes at least a portion of the system. The computing device is also configured to generate at least a second feature function with function input data based on a portion of the identified portion of the system input data for the first feature function. The computing device is further configured to determine an estimated error for each of the first feature function and the at least second feature function. The computing device is also configured to determine a final feature function based on the determined estimated errors. The computing device is further configured to generate a surrogate model for the system based on the mathematical representation of the system and the determined feature function.

In some examples, the computing device is configured to generate the at least second feature function by generating a second feature function with function input data based on a first portion of the identified portion of the system input data for the first feature function. The computing device also generates a third feature function with function input data based on a second portion of the identified portion of the system input data for the first feature function, wherein the second portion is different from the first portion.

In some examples, the computing device is configured to generate the at least second feature function by generating a first plurality of feature functions with function input data based on portions of the identified portion of the system input data for the first feature function. The computing device is also configured to identify a predetermined number of the first plurality of feature functions based on their corresponding estimated errors, identifies common portions of function input data for the first plurality of feature functions, and generates a second plurality of feature functions with function input data based on the common portions.

In some examples, the computing device is configured to generate the at least second feature function by determining, based on one or more machine learning algorithms, one or more weights to be applied to the portion of the identified portion of the system input data for the first feature function.

In some examples, the system is a steam reformer, and the mathematical representation identifies and characterizes a performance of the steam reformer. In some examples, the system input data identifies methanol and the system output data identifies reformate. In some examples, the first feature function is a heat transfer function. In some examples, the function input data identifies at least one physics function of the system.

In some examples, the computing device is configured to determine a plurality of weights of the at least one physics function, and adjust the plurality of weights based on the estimated error for each of the first feature function and the at least second feature function.

In some embodiments, a non-transitory computer readable medium has instructions stored thereon. The instructions, when executed by at least one processor, cause a device to perform operations that include identifying a mathematical representation of a system, and determining correlations between system input data and system output data of the system. The operations also include identifying at least a portion of the system input data based on the correlations. Further, the operations include generating a first feature function with function input data based on the identified portion of the system input data, wherein the original feature function characterizes at least a portion of the system. The operations also include generating at least a second feature function with function input data based on a portion of the identified portion of the system input data for the first feature function. The operations further include determining an estimated error for each of the first feature function and the at least second feature function. Further, the operations include determining a final feature function based on the determined estimated errors. The operations also include generating a surrogate model for the system based on the mathematical representation of the system and the determined feature function.

In some examples, generating the at least second feature function includes generating a second feature function with function input data based on a first portion of the identified portion of the system input data for the first feature function. The operations also include generating a third feature function with function input data based on a second portion of the identified portion of the system input data for the first feature function, wherein the second portion is different from the first portion.

In some examples, generating the at least second feature function includes generating a first plurality of feature functions with function input data based on portions of the identified portion of the system input data for the first feature function. The operations also include identifying a predetermined number of the first plurality of feature functions based on their corresponding estimated errors. Further, the operations include identifying common portions of function input data for the first plurality of feature functions, and generating a second plurality of feature functions with function input data based on the common portions.

In some examples, generating the at least second feature function includes determining, based on one or more machine learning algorithms, one or more weights to be applied to the portion of the identified portion of the system input data for the first feature function.

In some embodiments, a system includes a computing device configured to receive sensor data from an apparatus. The computing device is also configured to execute a surrogate model for the system, where the surrogate model is based on a mathematical representation of the system and a feature function. The computing device is further configured to determine a system state for the system based on the received sensor data and execution of the surrogate model, and provide for display the system state. For example, the computing device may display the system state.

In some examples, the apparatus includes at least one sensor, a transmitter, and at least one processor communicatively coupled to the at least one sensor and the transmitter. In some examples, the at least one processor is configured to receive sensor data from the sensor, and cause the transmitter to transmit the sensor data to the computing device.

In some examples, the computing device is configured to predict a future state of a component of the system based on the received sensor data and execution of the surrogate model.

In some examples, the computing device is configured to determine correlations between system input data and system output data of the system, and identify at least a portion of the system input data based on the correlations. The computing device is also configured to generate a first feature function with function input data based on the identified portion of the system input data, where the original feature function characterizes at least a portion of the system. The computing device is further configured to generate at least a second feature function with function input data based on a portion of the identified portion of the system input data for the first feature function. The computing device is also configured to determine an estimated error for each of the first feature function and the at least second feature function. Further, the computing device is configured to determine a final feature function based on the determined estimated errors. The computing device is also configured to generate the surrogate model for the system based on the mathematical representation of the system and the determined feature function.

In some examples, the computing device is configured to generate the at least second feature function by generating a second feature function with function input data based on a first portion of the identified portion of the system input data for the first feature function. The computing device is also configured to generate a third feature function with function input data based on a second portion of the identified portion of the system input data for the first feature function, wherein the second portion is different from the first portion.

In some examples, the computing device is configured to generate a first plurality of feature functions with function input data based on portions of the identified portion of the system input data for the first feature function. The computing device is further configured to identify a predetermined number of the first plurality of feature functions based on their corresponding estimated errors, and identify common portions of function input data for the first plurality of feature functions. The computing device is further also configured to generate a second plurality of feature functions with function input data based on the common portions.

In some examples, generating the at least second feature function includes determining, based on one or more machine learning algorithms, one or more weights to be applied to the portion of the identified portion of the system input data for the first feature function.

In some embodiments, a computing device configured to identify a mathematical representation of an exhaust manifold system, and determine correlations between exhaust manifold system input data and exhaust manifold system output data of the exhaust manifold system. The computing device is also configured to identify at least a first portion of the exhaust manifold system input data based on the correlations. Further, the computing device is configured to generate a first feature function with function input data based on the first portion of the exhaust manifold system input data, wherein the first feature function characterizes at least a portion of the exhaust manifold system. The computing device is further configured to generate at least a second feature function with function input data based on a portion of the first portion of the exhaust manifold system input data. The computing device is also configured to determine an estimated error for each of the first feature function and the at least second feature functions. Further, the computing device is configured to determine a final feature function based on the determined estimated errors. The computing device is also configured to generate a surrogate model for the exhaust manifold system based on the mathematical representation of the exhaust manifold system and the determined final feature function.

In some examples, the computing device is configured to generate the at least second feature function by generating a second feature function with function input data based on a first portion of the first portion of the system input data, and generating a third feature function with function input data based on a second portion of the first portion of the system input data, where the second portion of the first portion of the system input data is different from the first portion of the first portion of the system input data.

In some examples, the computing device is configured to generate the at least second feature functions by generating a first plurality of feature functions with function input data based on portions of the first portion of the system input data, where determining the estimated error for each of the first feature function and the at least second feature functions includes determining estimated errors for each of the first plurality of feature functions.

In some examples, the computing device is further configured to identify a predetermined number of the first plurality of feature functions based on their corresponding estimated errors, and identify common portions of function input data for the first plurality of feature functions. The computing device is further configured to generate a second plurality of feature functions with function input data based on the common portions of function input data for the first plurality of feature functions.

In some examples, generating the at least second feature function includes determining, based on one or more machine learning algorithms, one or more weights to be applied to the portion of the first portion of the system input data.

In some embodiments, a system includes a computing device that is configured to receive sensor data from an exhaust manifold system, and execute a surrogate model for the exhaust manifold system, wherein the surrogate model is based on a mathematical representation of the exhaust manifold system and a feature function. The computing device is also configured to determine a system state for the exhaust manifold system based on the received sensor data and execution of the surrogate model. In some examples, the computing device is configured to provide for display the system state. In some examples, the computing device displays the system state.

In some examples, the system includes at least one sensor, a transmitter, and, at least one processor communicatively coupled to the at least one sensor and the transmitter. The processor is configured to receive sensor data from the sensor, and cause the transmitter to transmit the sensor data to the computing device.

In some examples, the computing device is configured to predict a future state of a component of the exhaust manifold system based on the received sensor data and execution of the surrogate model.

In some examples, the computing device is configured to predict a life expectancy of a component of the exhaust manifold system based on the received sensor data and execution of the surrogate model.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A computing device configured to:
   identify a mathematical representation of a system;
   determine correlations between system input data and system output data of the system;
   identify at least a portion of the system input data based on the correlations;
   generate a first feature function with function input data based on the identified portion of the system input data, wherein the original feature function characterizes at least a portion of the system;
   generate at least a second feature function with function input data based on a portion of the identified portion of the system input data for the first feature function;
   determine an estimated error for each of the first feature function and the at least second feature function;
   determine a final feature function based on the determined estimated errors; and
   generate a surrogate model for the system based on the mathematical representation of the system and the determined feature function.

2. The computing device of claim 1, wherein generating the at least second feature function comprises:
   generating the at least second feature function with function input data based on a first portion of the identified portion of the system input data for the first feature function; and
   generating a third feature function with function input data based on a second portion of the identified portion of the system input data for the first feature function, wherein the second portion is different from the first portion.

3. The computing device of claim 1, wherein generating the at least second feature function comprises:
   generating a first plurality of feature functions with function input data based on portions of the identified portion of the system input data for the first feature function;
   identifying a predetermined number of the first plurality of feature functions based on their corresponding estimated errors;
   identifying common portions of function input data for the first plurality of feature functions; and
   generating a second plurality of feature functions with function input data based on the common portions.

4. The computing device of claim 1, wherein generating the at least second feature function comprises determining, based on one or more machine learning algorithms, one or more weights to be applied to the portion of the identified portion of the system input data for the first feature function.

5. The computing device of claim 1, wherein the system is a steam reformer, and the mathematical representation identifies and characterizes a performance of the steam reformer.

6. The computing device of claim 5, wherein the system input data identifies methanol and the system output data identifies reformate.

7. The computing device of claim 6 wherein the first feature function is a heat transfer function.

8. The computing device of claim 1 wherein the function input data identifies at least one physics function of the system.

9. The computing device of claim 8, wherein the computing device is configured to determine a plurality of weights of the at least one physics function, and adjust the plurality of weights based on the estimated error for each of the first feature function and the at least second feature function.

10. A non-transitory computer readable medium having instructions stored thereon, wherein the instructions, when executed by at least one processor, cause a device to perform operations comprising:
   identifying a mathematical representation of a system;
   determining correlations between system input data and system output data of the system;
   identifying at least a portion of the system input data based on the correlations;
   generating a first feature function with function input data based on the identified portion of the system input data, wherein the original feature function characterizes at least a portion of the system;
   generating at least a second feature function with function input data based on a portion of the identified portion of the system input data for the first feature function;
   determining an estimated error for each of the first feature function and the at least second feature function;
   determining a final feature function based on the determined estimated errors; and
   generating a surrogate model for the system based on the mathematical representation of the system and the determined feature function.

11. The non-transitory computer readable medium of claim 10 further comprising instructions stored thereon that, when executed by the at least one processor, further cause the device to perform operations comprising:
   generating the at least second feature function with function input data based on a first portion of the identified portion of the system input data for the first feature function; and
   generating a third feature function with function input data based on a second portion of the identified portion of the system input data for the first feature function, wherein the second portion is different from the first portion.

12. The non-transitory computer readable medium of claim 10 further comprising instructions stored thereon that, when executed by the at least one processor, further cause the device to perform operations comprising:
   generating a first plurality of feature functions with function input data based on portions of the identified portion of the system input data for the first feature function;
   identifying a predetermined number of the first plurality of feature functions based on their corresponding estimated errors;
   identifying common portions of function input data for the first plurality of feature functions; and
   generating a second plurality of feature functions with function input data based on the common portions.

13. The non-transitory computer readable medium of claim 10 wherein generating the at least second feature function comprises determining, based on one or more machine learning algorithms, one or more weights to be applied to the portion of the identified portion of the system input data for the first feature function.

14. A system comprising:
   a computing device configured to:
      determine correlations between system input data and system output data of the system;
      identify at least a portion of the system input data based on the correlations;
      generate a first feature with function input data based on the identified portion of the system input data, wherein the original feature function characterizes at least a portion of the system,
   generate at least a second feature function with function input data based on a portion of the identified portion of the system input data for the first feature function;
      determine an estimated error for each of the first feature function and the at least second feature function;
      determine a final feature function based on the determined estimated errors; and
      generate a surrogate model for the system based on the mathematical representation of the system and the determined feature function;
      receive sensor data from an apparatus;
      execute the surrogate model for the system;
      determine a system state for the system based on the received sensor data and the execution of the surrogate model; and
      display the system state.

15. The system of claim 14, wherein the apparatus comprises:
   at least one sensor;
   a transmitter; and
   at least one processor communicatively coupled to the at least one sensor and the transmitter, and configured to:
      receive sensor data from the sensor; and
      cause the transmitter to transmit the sensor data to the computing device.

16. The system of claim 14, wherein the computing device is configured to predict a future state of a component of the system based on the received sensor data and execution of the surrogate model.

17. The system of claim 14, wherein generating the at least second feature function comprises:
   generating the second feature function with function input data based on a first portion of the identified portion of the system input data for the first feature function; and
   generating a third feature function with function input data based on a second portion of the identified portion of the system input data for the first feature function, wherein the second portion is different from the first portion.

18. The system of claim 14, wherein generating the at least second feature function comprises:
   generating a first plurality of feature functions with function input data based on portions of the identified portion of the system input data for the first feature function;
   identifying a predetermined number of the first plurality of feature functions based on their corresponding estimated errors;
   identifying common portions of function input data for the first plurality of feature functions; and
   generating a second plurality of feature functions with function input data based on the common portions.

19. The system of claim 14, wherein generating the at least second feature function comprises determining, based on one or more machine learning algorithms, one or more weights to be applied to the portion of the identified portion of the system input data for the first feature function.

\* \* \* \* \*